(12) United States Patent
Simoneau

(10) Patent No.: US 6,420,359 B1
(45) Date of Patent: Jul. 16, 2002

(54) NON-NUCLEOSIDE REVERSE TRANSCRIPTASE INHIBITORS

(75) Inventor: Bruno Simoneau, Laval (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/879,447

(22) Filed: Jun. 12, 2001

Related U.S. Application Data

(60) Provisional application No. 60/256,638, filed on Dec. 18, 2000, and provisional application No. 60/212,329, filed on Jun. 16, 2000.

(51) Int. Cl.⁷ .................. C07D 471/14; A61K 31/55
(52) U.S. Cl. ........................... 514/220; 540/495
(58) Field of Search ............................ 540/495; 514/220

(56) References Cited

U.S. PATENT DOCUMENTS 5,366,972 A * 11/1994 Hargrave et al. ............ 514/220
5,705,499 A * 1/1998 Cywin et al. ................. 514/220

OTHER PUBLICATIONS

Hargrave, K. D., et al; Novel, Non–Nucleoside Inhibitors of HIV–1 Reverse Transcriptase. 1. Tricyclic Pyridobenzo- and Dipyridodiazepinones; J. Med. Chem. 1991, 34, 2231–2241.

\* cited by examiner

Primary Examiner—Bruck Kifle
(74) Attorney, Agent, or Firm—Robert P. Raymond; Alan R. Stempel; Mary-Ellen M. Devlin

(57) ABSTRACT

Provided are compounds of the general formula I:

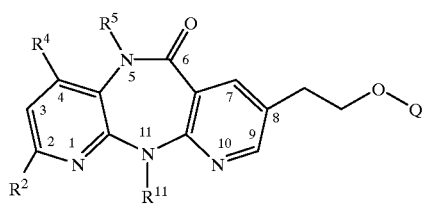

wherein
$R^2$ is selected from the group consisting of H, F, Cl, ($C_{1-4}$) alkyl, ($C_{3-4}$) cycloalkyl and $CF_3$; $R^4$ is H or Me; $R^5$ is H, Me or Et, with the proviso that $R^4$ and $R^5$ are not both Me, and if $R^4$ is Me then $R^5$ cannot be Et; $R^{11}$ is Et, cyclopropyl, propyl, isopropyl, or isobutyl; and
Q is selected from the group consisting of:

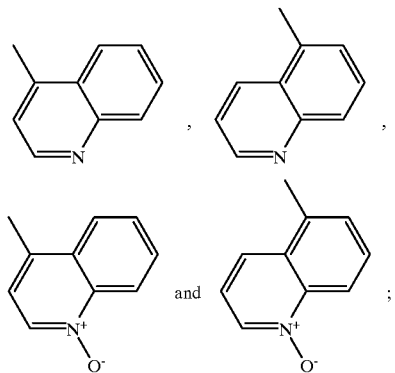

and pharmaceutically acceptable salts thereof, as inhibitors of HIV reverse transcriptase, wild-type and several mutant strains.

9 Claims, No Drawings

NON-NUCLEOSIDE REVERSE TRANSCRIPTASE INHIBITORS

RELATED APPLICATIONS

Benefit of U.S. Provisional Application Ser. No. 60/212,329, filed on Jun. 16, 2000, and U. S. Provisional Application Ser. No. 60/256,638, filed on Dec. 18, 2000, are hereby claimed.

TECHNICAL FIELD OF THE INVENTION

The invention relates to novel compounds and pharmaceutically acceptable as salts thereof, their use, either alone or in combination with other therapeutic agents, in the treatment or prophylaxis of HIV infection, and to pharmaceutical compositions comprising the compounds.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. The transcription of the viral RNA into DNA is accomplished by an enzyme that has been aptly dubbed reverse transcriptase (RT). The HIV virion includes a copy of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA.

Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz and Abacavir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterised, and resistance to known therapeutic agents is due to mutations in the RT gene. Some of the most commonly observed mutants clinically are: the Y181C mutant, in which a tyrosine (Y), at codon 181, has been mutated to a cysteine (C) residue, and K103N where the lysine (K) at position 103 has been replaced by asparagine (N). Other mutants which emerge with increasing frequency during treatment with known antivirals include the single mutants V106A, G190A, Y188C, and P236L; and the double mutants K103N/Y181C, K103N/P225H, K103N/V108I, and K103N/L100I.

As therapy and prevention of HIV infection using antivirals continues, the emergence of new resistant strains is expected to increase. There is therefore an ongoing need for new inhibitors of RT, with different patterns of effectiveness against the various mutants.

Compounds having tricyclic structures which are inhibitors of HIV are described in U.S. Pat. No. 5,366,972. Other inhibitors of HIV-1 reverse transcriptase are described in Hargrave et al., J. Med Chem., 34, 2231 (1991).

U.S. Pat. No. 5,705,499 proposes 8-arylalkyl- and 8-arylheteroalkyl-5,11-dihydro-6H-dipyrido[3,2-B:2',3'-E][1,4]diazepines as inhibitors of RT. The exemplified compounds are shown to have some activity against wild type and mutant HIV-1 RT, particularly Y181C and other single mutants such as K103N albeit less effectively.

Specifically, the compounds of the present invention are effective at inhibiting the Y181C and K103N mutants as well as a broad range of other single mutants and certain commonly found double mutants such as K103N/Y181C and K103N/P225H.

SUMMARY OF THE INVENTION

The invention reduces the difficulties and disadvantages of the prior art by providing novel compounds that are potent inhibitors of single and double mutant strains of HIV-1 RT.

In a first aspect the invention provides a compound of the general formula I:

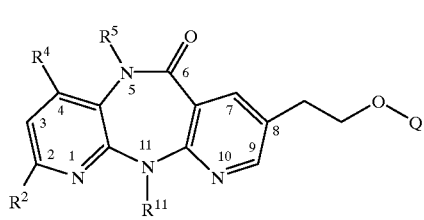

wherein $R^2$ is selected from the group consisting of H, F, Cl, $C_{1-4}$ alkyl, $C_{3-4}$ cycloalkyl and $CF_3$;

$R^4$ is H or Me;

$R^5$ is H, Me or Et, with the proviso that $R^4$ and $R^5$ are not both Me, and if $R^4$ is Me then $R^5$ cannot be Et;

$R^{11}$ is Me, Et, cyclopropyl, propyl, isopropyl, or cyclobutyl;

Q is selected from the group consisting of:

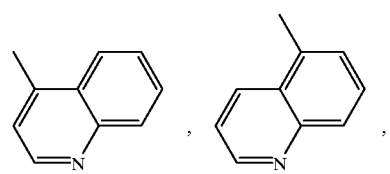

-continued

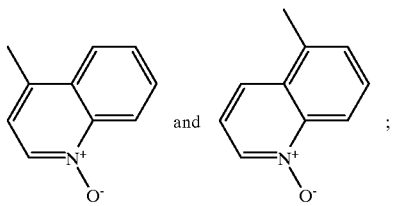

or a pharmaceutically acceptable salt thereof.

In a second aspect, the invention provides an inhibitor of HIV replication, of the general formula I, or a pharmaceutically acceptable salt thereof.

In a third aspect, the invention provides an inhibitor of a reverse transcriptase enzyme of HIV, of the general formula I, or a pharmaceutically acceptable salt thereof.

In a fourth aspect, the invention provides a method for the treatment or prevention of HIV infection, comprising administering to a patient an HIV inhibiting amount of a compound of formula IL or a pharmaceutically acceptable salt thereof.

In a fifth aspect, the invention provides a pharmaceutical composition for the treatment or prevention of HIV infection, comprising a compound of formula I, or a pharmaceutically acceptable salt thereof, and a pharmaceutically acceptable carrier.

In a sixth aspect, the invention provides a method for preparation of a compound of formula I, or a pharmaceutically acceptable salt thereof.

DETAILED DESCRIPTION OF THE INVENTION

Definitions

As used herein, the term "$C_{3-4}$ alkyl" is intended to mean linear or branched alkyl radicals containing from one to four carbon atoms and includes methyl, ethyl, propyl, isopropyl, butyl, sec-butyl and tert-butyl.

As used herein, the term "$C_{3-4}$ cycloalkyl" is intended to mean saturated cyclic hydrocarbon radicals containing three to four carbon atoms and includes cyclopropyl and cyclobutyl.

DETAILED DESCRIPTION OF PREFERRED EMBODIMENT

According to a preferred embodiment, compounds of the invention are defined according to formula I wherein $R^2$ is preferably Cl, F, or H. More preferably, $R^2$ is Cl or H. Most preferably, $R^2$ is H.

According to a preferred embodiment, compounds of the invention are defined according to formula I wherein $R^4$ is preferably H.

According to an alternative embodiment, compounds of the invention are defined according to formula I wherein preferably $R^5$ is Me.

Preferably, compounds of the invention are defined according to formula I wherein $R^{11}$ is Et or cyclopropyl. More preferably, $R^{11}$ is Et.

According to a preferred embodiment, compounds of the invention are defined according to formula I wherein Q is preferably selected from the group consisting of:

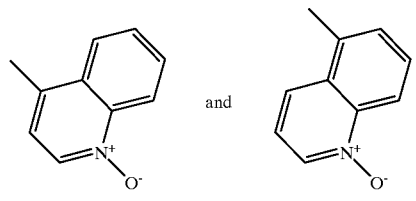

More preferably, Q is:

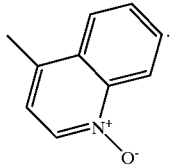

Alternatively, preferred embodiments of the invention include compounds selected from the group consisting of:

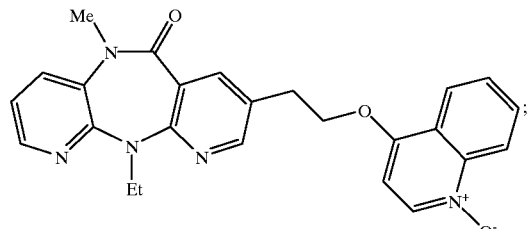

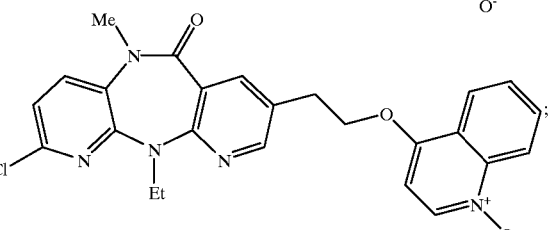

and

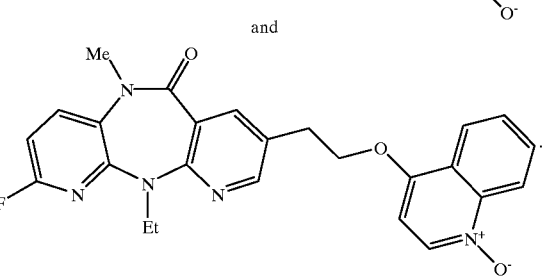

The compounds of the invention are effective inhibitors of wild type reverse transcriptase as well as inhibiting, for example, the single mutation enzymes Y181C, K103N, V106A, G190A, Y188C, and P236L. The compounds also inhibit the double mutation enzymes K103N/Y181C, K103N/P225H, K103N/V108I and K103N/L100I.

The compounds of formula I possess inhibitory activity against HIV-1 reverse transcriptase. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a novel compound of formula I, as described above. Whether it be termed treatment or prophylaxis, the compounds may also be used to prevent perinatal transmission of HIV-1 from mother to baby, by administration to the mother prior to birth.

The compounds of formula I may be administered in single or divided doses by the oral or parenteral routes. A suitable oral dosage for a compound of formula I would be in the range of about 0.5 mg to 1 g per day. A preferred oral dosage for a compound of formula I would be in the range of about 100 mg to 800 mg per day for a patient weighing 70 kg. In parenteral formulations, a suitable dosage unit may contain from 0.1 to 250 mg of said compounds, preferably 1 mg to 200 mg. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations, which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilisation. Further, the pharmaceutical preparations may contain conventional adjuvants such as preservatives, stabilisers, emulsifiers, flavour-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chlorobutanol or phenylethyl alcohol.

Additionally, the compounds provided by the invention can be administered by suppository.

The compounds of the invention may be made using the skills of a synthetic organic chemist. An exemplary reaction scheme is shown in schemes 1 to 6.

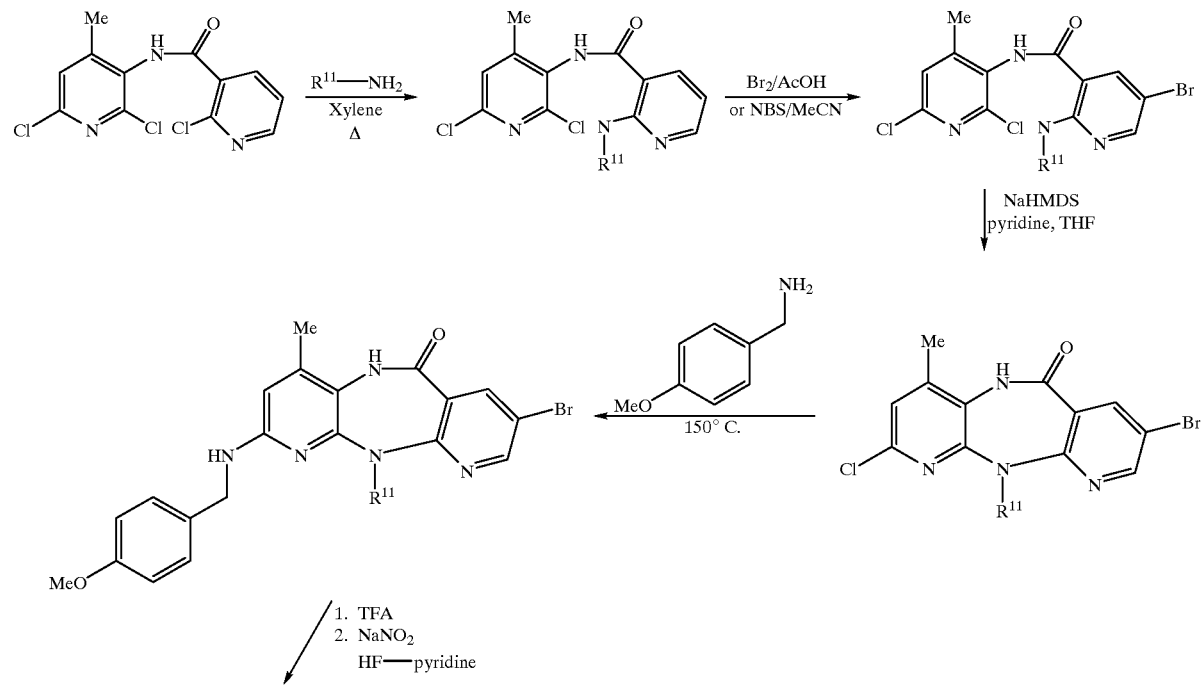

Scheme 1
Preparation of intermediates in which $R^4$ is Me

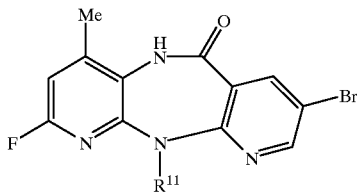
-continued
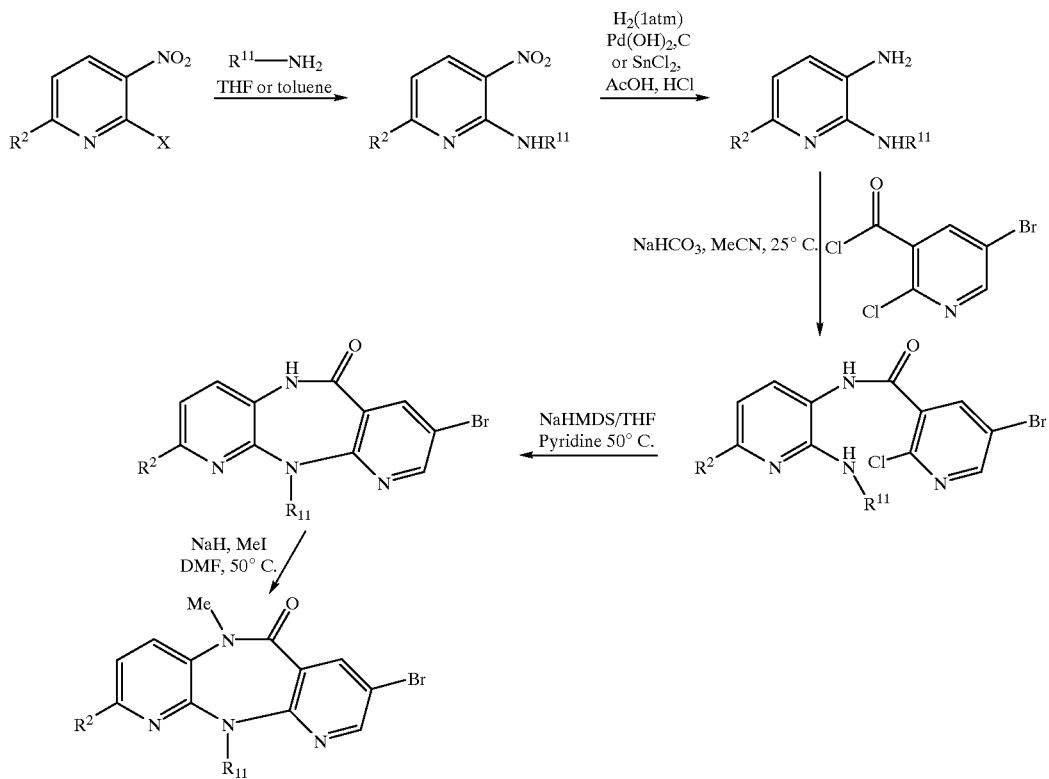
The sequence of scheme 2 is analogous to one described by J. M. Klunder et al.; *J. Med. Chem.* 1998, 41, 2960–71, and C. L. Cywin et al.; *J. Med. Chem.* 1998, 41, 2972–84.
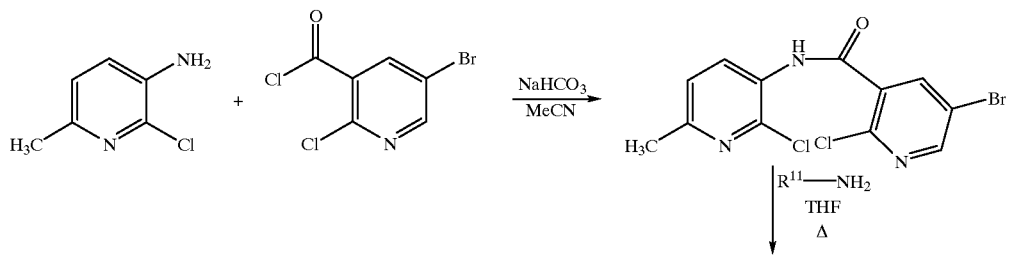

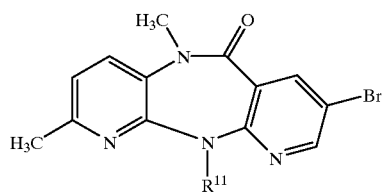
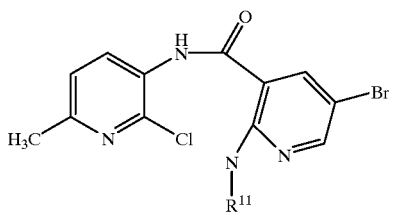
Scheme 4: Preparation of intermediates in which $R^2$ is $CF_3$
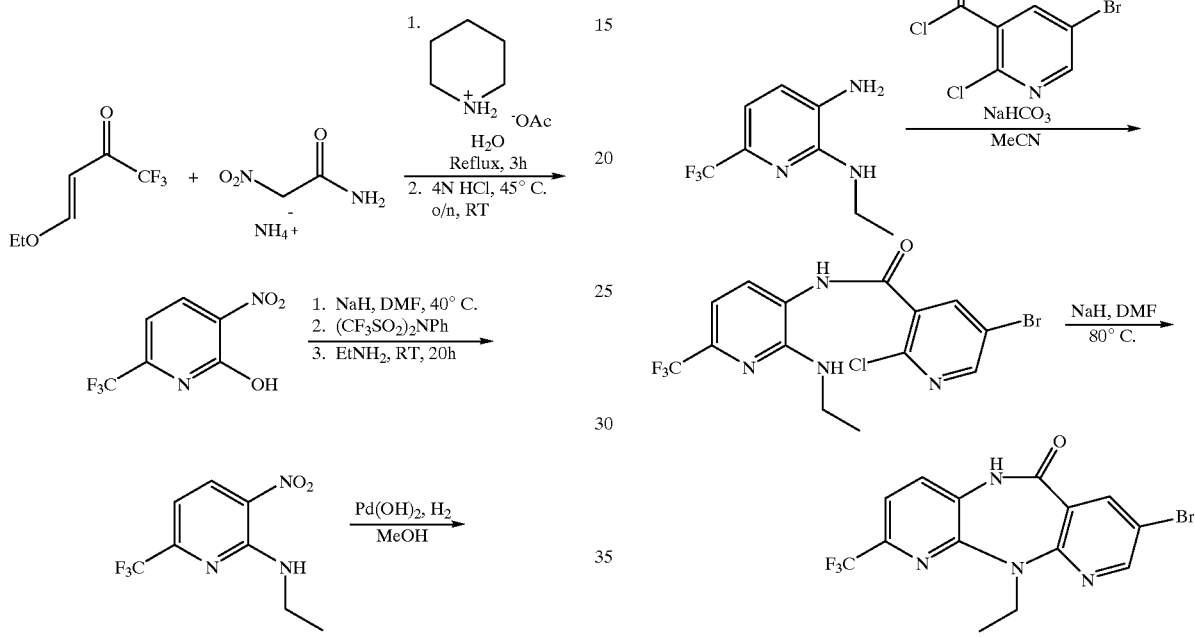
Scheme 5: Introduction of the quinoline nucleus
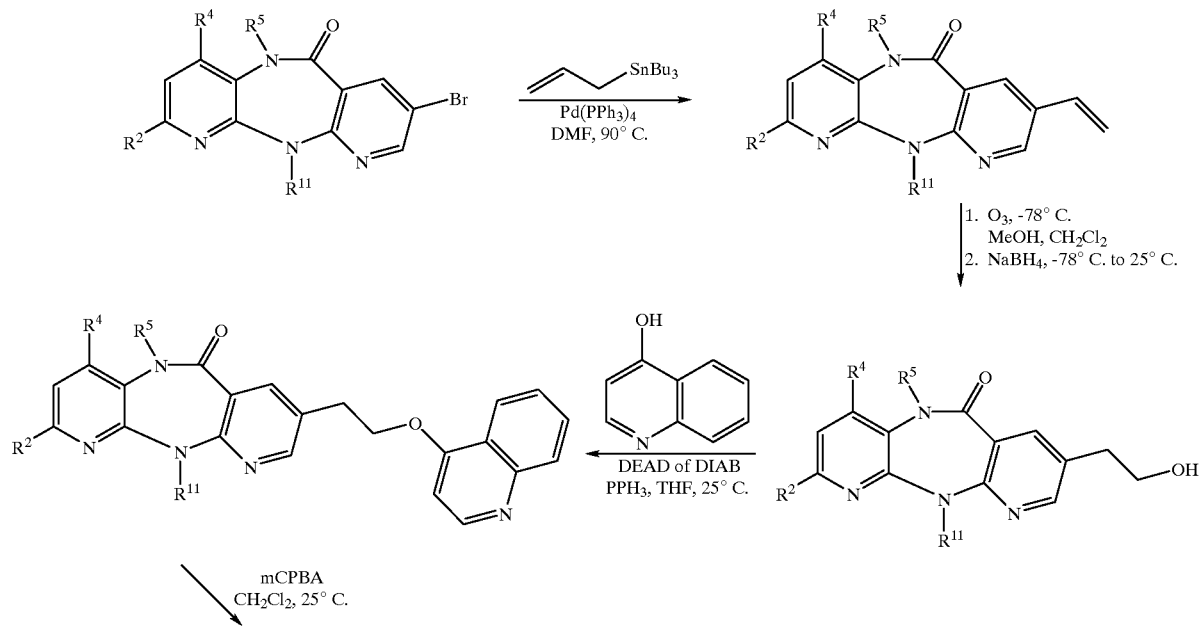

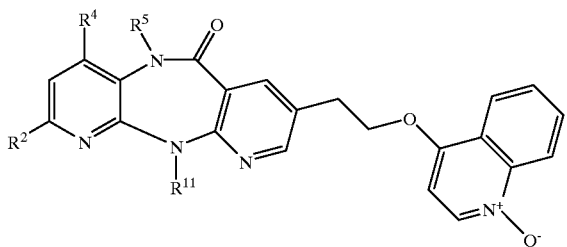

-continued

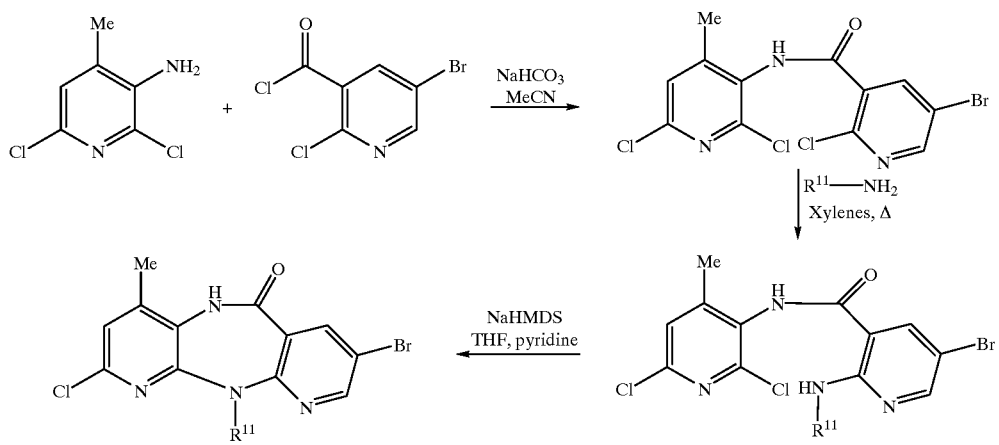

Scheme 6: Alternate route of compounds in which R⁴ is Me

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT. Utilising the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table 2 as $IC_{50}$ (nM) and Table 3 as ECso (nM).

EXAMPLES

The present invention is illustrated in further detail by the following non-limiting examples. All reactions were performed in a nitrogen or argon atmosphere. Temperatures are given in degrees Celsius. Solution percentages or ratios express a volume to volume relationship, unless stated otherwise.

Abbreviations or symbols used herein include:

DEAD: diethyl azodicarboxylate;
DIAD: diisopropyl azodicarboxylate;
DIEA: diisopropylethylamine;
DMAP: 4(dimethylamino)pyridine;
DMSO: dimethylsulfoxide;
DMF: dimethylformamide;
ES MS: electron spray mass spectrometry;
Et: ethyl;
EtOAc: ethyl acetate;
$Et_2O$: diethyl ether;
HPLC: high performance liquid chromatography;
iPr: isopropyl;
Me: methyl;
MeOH: methanol;
MeCN: acetonitrile;
NBS: N-bromosuccinimide;
Ph: phenyl;
TBE: tris-borate-EDTA;
TBTU: 2-(1H-benzotriazol-1-yl)-N,N,N',N'-tetramethyluronium tetrafluoroborate;
TFA: trifluoroacetic acid;
THF: tetrahydrofuran;
MS (ES): electrospray mass spectrometry;
MS (FAB) or FAB/MS: fast atom bombardment mass spectrometry;
HRMS: high resolution mass spectrometry;
PFU: plaque forming units;
DEPC: diethyl pyrocarbonate;
DTT: dithiothreitol;
EDTA: ethylenediaminetetraacetate;
UMP: uridine 5'-monophosphate;
UTP: uridine 5'-triphosphate;
MES: 2-(n-morpholino)ethanesulfonic acid;
SDS-PAGE: sodium dodecyl sulfate-polyacrylamide gel electrophoresis;
MWCO: molecular weight cut-off;

Bis-Tris Propane: 1,3-Bis{tris(hydroxymethyl)-methylamino}propane;

GSH: reduced glutathione;

OBG: n-Octyl-β-D-glucoside.

SYNTHESES

The following examples illustrate methods for preparing compounds of the invention.

Example I (Entry 24, Table 1)

5,11-Dihydro-11-ethyl-5-methyl-8-{2-(4-quinolinytoxy)ethyl}-6H-dipyrido[3,2-b:2',3'-e][1,4]diazepin-6-one a) 2-(Ethylamino)-3-nitropyridine To a solution of 2-chloro-3-nitropyridine (51 g, 325 mmol) in THF (650 mL) was added a 2 M solution of ethylamine in THF (365 mL, 731 mmol). The reaction was stirred at room temperature overnight. The reaction mixture was poured into water (~1.5 L) and the resulting solid was filtered and dried under reduced pressure to give the title compound (52 g).

b) 3-Amino-2-(ethylamino)pyridine

A solution of 2-(ethylamino)-3-nitropyridine (52 g) in MeOH (600 mL) was stirred overnight at room temperature under hydrogen (1 atm.) in the presence of 20% Pd(OH)$_2$/C (10.4 g). The catalyst was removed by filtration through diatomaceous earth. The filtrate was concentrated under reduced pressure to give the title compound as a black solid (39 g, 88% yield over steps a) and b)).

c) 2-Chloro-N-{2-(ethylamino)-3-pyridinyl}-5-bromo-3-pyridinecarboxamide

To a cooled solution of 3-amino-2-(ethylamino)pyridine (30.6 g, 223 mmol) in MeCN (740 mL) was added solid NaHCO$_3$ (56.3 g, 669 mmol). After 5 min, crude 5-bromo-2-chloro-3-pyridinecarbonyl chloride (prepared from 5-bromo-2-hydroxy-3-pyridinecarboxylic acid and SOCl$_2$ [as described by T. W. Gero et al. in *Synth. Commun.* 1989, 19, 553–559 (incorporated herein by reference) but with omission of the aqueous work-up] was added (1 equiv., 223 mmol). After 2 h, the reaction mixture was poured over ice/H$_2$O (1.5 L) and the resulting solid was filtered, rinsed with H$_2$O and then hexane. After drying under reduced pressure overnight, the title compound was obtained as a black solid (54.9 g, 69% yield).

d) 8-Bromo-5,11-dihydro-11-ethyl-6H-dipyrido[3,2-b:2',3'-e][1,4]diazepin-6-one

To a solution of 2-chloro-N-{2-(ethylamino)-3-pyridinyl}-5-bromo-3-pyridinecarboxamide (54.9 g, 154.4 mmol) in pyridine (308 mL) at 50° C. was added drop-wise a 1 M solution of NaHMDS (sodium hexamethyldisilazide) in THF (355 mL, 355 mmol). After 10 min, the reaction was allowed to cool to room temperature, and then was poured over ice water (2 L). The resulting solid was filtered, rinsed with water and then hexane. The solid was dried under reduced pressure to give the title compound (36 g, 75% yield) as a dark green solid.

e) 8-Bromo-5,11-dihydro-11-ethyl-5-methyl-6H-dipyrido[3,2-b:2',3'e][1,4]diazepin-6-one To a solution of the 8-bromo-5,11-dihydro-11-ethyl-6H-dipyrido[3,2-b:2',3'-e] [1,4]diazepin-6-one (36.7 g, 115 mmol) in DMF (380 mL) was added NaH (3.5 g, 138 mmol), and the mixture was heated to 50° C. for 30 min. The reaction mixture was cooled to room temperature and treated with MeI (14.3 mL, 230 mmol). After 1.5 h, the reaction mixture was poured over ice water. The solid was filtered, washed with water and then hexane to give after drying the title compound (37.9 g 99% yield) as a dark grey solid.

f) 5,11-Dihydro-11-ethyl-5-methyl-8-(2-propenyl)-6H-dipyrido[3,2-b:2',3'e][1,4]diazepin-6one Allyltributyltin (30.7 mL, 99.0 mmol) and Pd(Ph$_3$P)$_4$ (5.20 g, 4.50 mmol) were added to a degassed (N$_2$ through solution for 30 min) solution of 8-bromo-5,11-dihydro-11-ethyl-5-methyl-6H-dipyrido[3,2-b:2',3'-e][1,4]diazepin-6-one (30.0 g, 90.0 mmol) in DMF (450 mL) at room temperature. The mixture was stirred at 90° C. for 1.5 h then was cooled to room temperature and concentrated under reduced pressure. The residue was purified by flash chromatography (hexane: EtOAc, 8:2 to 7:3) to give the title compound (22.19 g, 84% yield).

g) 5,11-Dihydro-11-ethyl-8-(2-hydroxyethyl)-5-methyl-6H-dipyrido[3,2-b:2',3'e][1,4]diazepin-6-one A stream of ozonised oxygen was bubbled through a cold (−78° C.) solution of 5,11-dihydro-11-ethyl-5-methyl-8-(2-propenyl)-6H-dipyrido[3,2-b:2',3'-e][1,4]diazepin-6-one (22.19 g, 75.4 mmol) in CH$_2$Cl$_2$ (150 mL) and MeOH (150 mL) for 2.5 h. A stream of N$_2$ was next bubbled through the solution for 15 min and then solid NaBH$_4$ (4.99 g, 132 mmol) was added to the solution. The reaction mixture was allowed to warm to room temperature. After 1 h, aqueous saturated NH$_4$Cl (200 mL) was added and the mixture was stirred at room temperature for 2 h. The organic solvents were removed under reduced pressure. Water (300 mL) and CHCl$_3$ (300 mL) were added to the residue. The phases were separated and the aqueous layer was extracted with CHCl$_3$ (3×300 mL). The combined organic layers were dried (MgSO$_4$), filtered and concentrated under reduced pressure. The residue was purified by flash chromatography (EtOAc:CHCl$_3$, 4:1) to give the title compound (16.1 g, 72% yield) as a white solid.

h) 5,11-Dihydro-11-ethyl-5-methyl-8-{2-(4-quinolinyloxy)ethyl}-6H-dipydo[3,2b:2',3'-e][1,4]diazepin-6-one Diethyl azodicarboxylate (DEAD) (12.8 mL, 81.0 mmol) was added drop-wise to a solution of 5,11-dihydro-11-ethyl-8-(2-hydroxyethyl)-5-methyl-6H-dipyrido[3,2-b:2',3'-e][1,4]diazepin-6-one (16.1 g, 54.0 mmol), 4-hydroxyquinoline (11.6 g, 81.0 mmol) and Ph$_3$P (21.3 g, 81.0 mmol) in THF (270 mL) at room temperature. The mixture was stirred at room temperature for 1h then was concentrated under reduced pressure. The residue was purified by flash chromatography (EtOAc:MeOH; 95:5) to give the title compound (17.7 g, 77% yield) as a white solid: MS (ESI) m/z 426 (MH)$^+$.

Example II (Entry 2, Table 1)

2-Chloro-5,11-dihydro-11-ethyl-5-methyl-8-{2-(4-quinolinyloxy)ethyl}-6H-dipyrido[3,2-b:2',3'-e][1,4]diazepin-6-one a) 6-Chloro-2-(ethylamino)-3-nitropyridine An ice-cold solution of EtNH$_2$ (49.8 g, 1.10 mol) in toluene (200 mL) was added over 15 min to an ice-cold solution of 2,6-dichloro-3-nitropyridine (100.0 g, 0.52 mol) in toluene (225 mL). The mixture was stirred at 0° C. for 45 min. Water (500 mL) and EtOAc (500 mL) were added and the phases were separated. The organic layer was successively washed with water (200 mL) and brine (200 mL), dried (MgSO$_4$), filtered and concentrated under reduced pressure. The residual solid was recrystallised from MeOH to give the title compound (83.7 g, 80% yield) as yellow needles.

b) 3-Amino-6chloro-2-(ethylamino)pyridine

A solution of $SnCl_2.H_2O$ (616.3 g, 2.73 mol) in aqueous 12 N HCl (500 mL) was rapidly added to a solution of 6-chloro-2-(ethylamino)-3-nitropyridine (169.5 g, 0.84 mol) in AcOH (1.7 L) at room temperature. After 20 min, the mixture was cooled to 0° C. and water (250 mL) was added. Solid NaOH (240 g) was then added in small portions. The resulting suspension was filtered to remove tin salts. The filtrate was diluted with water (3.5 L), the solution rendered basic by addition of aqueous 10 N NaOH and then extracted with EtOAc (3×1.7 L). The combined organic layers were washed with brine (1 L), dried ($MgSO_4$), filtered and concentrated under reduced pressure. The residue was purified by flash chromatography (hexane:EtOAc, 3:2) to give the title compound (89.9 g, 62% yield) as a brown solid: MS (ESI) m/z 172/174 $(MH)^+$.

c) 5-Bromo-2-chloro-N-{2-(ethylamino)-6-chloro-3-pyridinyl}-3 pyridinecarboxamide A solution of 5-bromo-2-chloro-3-pyridinecarbonyl chloride (30.0 g, 97.0 mmol) in MeCN (100 mL) was added via cannula to a solution of 3-amino-6-chloro-2-(ethylamino) pyridine (16.6 g, 97.0 mmol) in MeCN (180 mL) containing solid $NaHCO_3$ (14.2 g, 169 mmol) at room temperature. The mixture was stirred at room temperature for 1 h. Water (200 mL) was added and the mixture was stirred for 10 min. The resulting suspension was filtered. The solid was washed with $Et_2O$ (50 mL) and concentrated from pyridine solution (3×50 mL) to give the title compound (28.4 g, 75% yield).

d) 8-Bromo-2-chloro-5,11-dihydro-11-ethyl-6H-dipyrido[3,2-b:2',3'-e][1,4]diazepin-6-one A 1 M solution of NaHMDS in THF (167.5 mL, 167.5 mmol) was slowly added to a solution of 5-bromo-2-chloro-N-{2-(ethylamino)-6-choro-3-pyridinyl}-3-pyridinecarboxamide (28.4 g, 72.8 mmol) in pyridine (146 mL) heated to 50° C. The reaction mixture was stirred at 50° C. for 1.5 h. The mixture was then poured into a mixture of water and ice (1 L) and, after 1 h, the resulting suspension was filtered. The solid was washed with water and dried under reduced pressure to give the title compound (23.4 g, 91% yield).

e) 8-Bromo-2-chloro-5,11-dihydro-11-ethyl-5-methyl-6H-dipyrido[3,2-b:2',3'-e][1,4]diazepin-6-one Solid NaH (60% oil dispersion, 3.46 g, 86.1 mmol) was added over 30 min to a solution of 8-bromo-2-chloro-5,11-dihydro-11-ethyl-6H-dipyrido[3,2-b:2',3'-e] [1,4]diazepin-6-one (23.4 g, 66.3 mmol) in DMF (220 mL) at 50° C. The mixture was stirred at 50° C. for 1 h then was allow to cool to room temperature. The mixture was poured into water (1 L) and the resulting suspension was filtered. The solid was successively washed with water and hexane then dried under reduced pressure to give the title compound (23.0 g, 94% yield).

f) 2-Chloro-5,11-dihydro-11-ethyl-5-methyl-8-(2-propenyl)-6H-dipyrido[3,2-b:2',3'-e][1,4]diazepin-6-one Allyltributyltin (21.3 mL, 68.7 mmol) and $Pd(Ph_3P)_4$ (3.61 g, 3.12 mmol) were added to a degassed ($N_2$ through solution for 30 min) solution of 8-bromo-2-chloro-5,11-dihydro-11-ethyl-5-methyl-6H-dipyrido[3,2-b:2',3'-e] [1,4] diazepin-6-one (23.0 g, 62.5 mmol) in DMF (312 mL). The mixture was heated to 90° C. for 2 h. The mixture was concentrated under reduced pressure. The residue was purified by flash chromatography (hexane:EtOAc, 7:3) to give the title compound (13.4 g, 65% yield).

g) 2-Chloro-5,11-dihydro-11-ethyl-8-(2-hydroxyethyl)-5-methyl-6H-dipyrido[3,2-b:2',3'-e][1,4]diazepin-6-one Ozonised oxygen was introduced into a cold (−78° C.) solution of 2-chloro-5,11-dihydro-11-ethyl-5-methyl-8-(2-propenyl)-6H-dipyrido[3,2-b:2',3'-e] [1,4]diazepin-6-one (13.4 g, 40.7 mmol) in MeOH (102 mL) and $CH_2Cl_2$ (102 mL) until complete disappearance of the alkene. Nitrogen was bubbled through the solution to remove excess $O_3$. Solid $NaBH_4$ (2.69 g, 71.1 mmol) was next added in small portions and the mixture was allowed to warm slowly to room temperature. After 1 h, aqueous saturated $NH_4Cl$ (150 mL) was added and the mixture stirred for 20 min. The organic solvents were removed under reduced pressure. Water (100 mL) was added to the aqueous solution. The solution was extracted with CHCl3 (3×200 mL). The combined organic layers were dried ($MgSO_4$), filtered and concentrated under reduced pressure. The residue was purified by flash chromatography ($EtOAc:CHCl_{3, 4:1}$) to give the title compound (10.4 g, 77% yield).

h) 2-Chloro-5,11-dihydro-11-ethyl-5-methyl-8-{2-(4-quinolinyloxy)ethyl}-6H-dipyrido[3,2-b:2',3'-e] [1,4] diazepin-6-one Diethyl azodicarboxylate (DEAD) (4.26 mL, 27.0 mmol) was added drop-wise to a solution of 2-chloro-5,11-dihydro-11-ethyl-8-(2-hydroxyethyl)-5-methyl-6H-dipyrido[3,2-b:2',3'-e][1,4]diazepin-6-one (6.00 g, 18.0 mmol), 4-hydroxyquinoline (3.92 g, 27.0 mmol) and $Ph_3P$ (7.09 g, 27.0 mmol) in THF (90 mL) at room temperature. The mixture was stirred at room temperature for 1 h then was concentrated under reduced pressure. The residue was purified by flash chromatography (EtOAc:MeOH, 95:5) to give the title compound (6.22 g, 75% yield) as a white solid: MS (ESI) m/z 460/462.

Example III (Entry 6, Table 1)

2-Chloro-11-cyclopropyl-5,11-dihydro-5-methyl-8-{2-(4-quinolinyloxy)-ethyl}-6H-dipyrido[3,2-b:2',3'-e][1,4]diazepin-6-one a) 6-Chloro-2-(cyclopropylamino)-3-nitropyridine A solution of cyclopropylamine (1.25 g, 22.0 mmol) in toluene (11 mL) was added over 10 min to an ice-cold solution of 2,6-dichloro-3-nitropyridine (2.00 g, 10.4 mmol) in toluene (10 mL). The mixture was stirred at 0° C. for 1 h and at room temperature for 2 h. Water (50 mL) was added to the mixture and the phases were separated. The organic layer was washed with brine (25 mL), dried ($MgSO_4$), filtered and concentrated under reduced pressure. The residue was purified by flash chromatography (hexane:EtOAc, 3:2) to give the title compound (1.97 g, 89% yield) as a yellow solid.

b) 2-Chloro-11-cyclopropyl-5,11-dihydro-8-(2-hydroxyethyl)-5-methyl-6H-dipyrido[3,2-b:2',3'-e][1,4] diazepin-6-one The title compound was prepared from 6-chloro-2-(cyclopropylamino)-3-nitropyridine using a method similar to that described for the 11-ethyl analog in example II.

c) 2-Chloro-11-cyclopropyl-5,11-dihydro-5-methyl-8-{2-(4-quinolinyloxy)ethyl}-6H-dipyrido[3,2-b:2',3'-e][1,4] diazepin-6-one Diethyl azodicarboxylate (DEAD) (85.6 µL, 0.54 mmol) was added dropwise to a solution of 2-chloro-11-cyclopropyl-5,11-dihydro-8-(2-hydroxyethyl)-5-methyl-6H-dipyrido[3,2-b:2',3'-e] [1,4]diazepin-6-one (125 mg, 0.36 mmol), 4-hydroxyquinoline (78.9 mg, 0.54 mmol) and $Ph_3P$ (143 mg, 0.54 mmol) in THF (1.8 mL) at room temperature. The mixture was stirred at room temperature for 3 h then was concentrated under reduced pressure. The residue was partially purified by flash chromatography (EtOAc:MeOH; 95:5). The solid was further purified by reverse phase HPLC (CombiPrep ADS-AQ 50×20 mm, 5 μ, 120 A, 5–100% MeCN+0.10% TFA/water+0.10% TFA in 25 min) to give the trifluoroacetic acid salt of the title compound (17.7 g, 77% yield) as a white solid: MS (ESI) m/z 472/474 (MH)$^+$.

Example IV (Entry 4, Table 1)

5,11-Dihydro-11-ethyl-2-fluoro-5-methyl-8-{2-(4-quinolinyloxy)ethyl}-6H-dipyrido[3,2-b:2',3'-e][1,4]diazepin-6-one a) 2,6-Difluoro-3-nitropyridine To a mixture of concentrated sulphuric acid (600 mL) and fuming nitric acid (90%, 400 mL) in a ice-bath (internal temperature maintained at 5–10° C.) was added drop-wise 2,6-difluoropyridine (200 g, 1.74 mol). The resulting mixture was stirred overnight at room temperature. The mixture was poured slowly into 3 kg of ice and extracted with Et$_2$O (2×2 L). The combined organic layers were washed with aqueous 1.5 N NaOH (2×1 L), then with aqueous saturated NaHCO$_3$ (400 mL) or until pH is around 8–9. The organic layers were dried over MgSO$_4$, filtrated and concentrated under reduced pressure until constant weight (to remove unreacted 2,6-difluoropyridine: 10–12%). The title compound was obtained as a yellow liquid (207.3 g, 74% yield).

b) 2-(Ethylamino)-6fluoro-3-nitropyridine

To a solution of 2,6-difluoro-3-nitropyridine (45.7 g, 285 mmol) in THF (500 mL) at −40° C. was added drop-wise a solution of ethylamine (25.7 g, 570 mmol) in THF (250 mL). After 30 min, the reaction mixture was concentrated under reduced pressure and the residue was dissolved in EtOAc. The organic phase was washed with brine, dried (MgSO$_4$), filtered and concentrated. The resulting yellow solid was purified by flash chromatography (15% EtOAc in hexane) to give the title compound (43.2 g, 82% yield) as a yellow solid.

c) 3-Amino-2-(ethylamino)-6-fluoropyridine

A solution of 2-(ethylamino)-6-fluoro-3-nitropyridine (43.2 g, 230 mmol) in THF (1 L) was stirred overnight at room temperature under hydrogen (1 atm.) in the presence of 20% Pd(OH)$_2$/C (4.35 g). The catalyst was removed by filtration through diatomaceous earth. The filtrate was concentrated under reduced pressure to give the title compound (36.3 g, 95% yield) as a black solid.

d) 2-Chloro-N-{2-(ethylarnino)-6-fluoro-3pyridinyl}-5-bromo-3-pyridinecarboxamide To a cooled solution (4° C.) of 3-amino-2-(ethylamino)-6-fluoropyridine (31.0 g, 200 mmol) in MeCN (160 mL) was added solid NaHCO$_3$ (50.4 g, 600 mmol). After 15 min, a solution of 5-bromo-2-chloro-3-pyridinecarbonyl chloride (1 equiv., 200 mmol) in MeCN (155 mL) was added. After 60 min at room temperature, the reaction mixture was poured into water (1.2 L) and stirred for 30 min. The resulting solid was filtered, dried under reduced pressure at 50° C. overnight. The title compound (73.7 g, 99% yield) was obtained as a black solid.

e) 8-Bromo-5,11-dihydro-11-ethyl-2-fluoro-6H-dipyrido[3,2-b:2',3'-e][1,4]diazepin-6-one To a solution of the 2-chloro-N-{2-(ethylamino)-6-fluoro-3-pyridinyl}-5-bromo-3-pyridinecarboxamide (73.5 g, 216 mmol) in pyridine (435 mL) at 50° C. was added drop-wise a 1 M solution of NaHMDS in THF (520 mL, 520 mmol). After 10 min, the reaction was allowed to cool to room temperature, then poured over ice water (2 L). The resulting solid was filtered, rinse with water and then hexane. The solid was dried under reduced pressure to give the title compound (50.6 g, 69% yield) as a dark green solid.

f) 8-Bromo-5,11-dihydro-11-ethyl-2-fluoro-5-methyl-6H-dipyrido[3,2-b:2',3'-e][1,4]diazepin-6-one To a solution of the 8-bromo-5,11-dihydro-11-ethyl-2-fluoro- 6H-dipyrido[3,2-b:2',3'-e][1,4]diazepin-6-one (44 g, 130.5 mmol) in DMF (520 mL) was added NaH (4.28 g, 178 mmol), and the mixture was heated to 50° C. for 30 min. The reaction mixture was cooled to room temperature and treated with MeI (24.4 mL, 522 mmol). After 1.5 h, the reaction mixture was poured over ice water. The solid was filtered, washed with water and then hexane, dried under reduced pressure to give the title compound (43.2 g, 94% yield) as dark grey solid.

g) 5,11-Dihydro-11-ethyl-2-fluoro-5-methyl-8-(2-propenyl)-6H-dipyrido[3,2-b:2',3'-e][1,4]diazepin-6-one Allyltributyltin (32.0 mL, 103.4 mmol) and Pd(Ph$_3$P)$_4$ (5.43 g, 4.70 mmol) were added to a degassed (N$_2$ through solution for 45 min) solution of 8-bromo-5,11-dihydro-11-ethyl-2-fluoro-5-methyl-6H-dipyrido[3,2-b:2',3'-e][1,4]diazepin-6-one (33.0 g, 94.0 mmol) in DMF (470 mL). Additional amounts of Pd(Ph$_3$)$_4$ (1.09 g, 0.94 mmol added after 1, 2,3,4,5 h of reaction) were added to complete the reaction. The mixture was heated to 90° C. for 6 h. The mixture was concentrated under reduced pressure. The residue was purified by flash chromatography (hexanes:EtOAc, 8:2 to 7:3) to give the title compound (22.4 g, 76% yield).

h) 5,11-Dihydro-11-ethyl-2-fluoro-8-(2-hydroxyethyl)-5-methyl-6H-dipyrido[3,2-b:2',3'-e][1,4]diazepin-6-one A stream of ozonised oxygen was bubbled through a cold (−78° C.) solution of 5,11-dihydro-11-ethyl-2-fluoro-5-methyl-8-(2-propenyl)-6H-dipyrido[3,2-b:2',3'-e][1,4]diazepin-6-one (22.38 g, 71.6 mmol) in CH$_2$Cl$_2$ (100 mL) and MeOH (100 mL) for 3 h. A stream of N$_2$ was next bubbled through the solution for 15 min and then solid NaBH$_4$ (5.05 g, 133 mmol) was added to the solution. The reaction mixture was allowed to warm to room temperature. After 1 h, an additional portion of NaBH$_4$ (1.62 g, 43.0 mmol) was added to the reaction mixture. After an additional hour, aqueous saturated NH$_4$Cl (150 mL) was added and the mixture was stirred at room temperature for 30 min. The organic solvents were removed under reduced pressure. Water (200 mL) was added and the mixture was extracted with CHCl$_3$ (3×300 mL). The combined organic layers were dried (MgSO$_4$), filtered and concentrated under reduced pressure. The residue was purified by flash chromatography (EtOAc:CHCl$_3$, 4:1) to give the title compound (19.7 g, 72% yield) as a white solid.

i) 5,11-Dihydro-11-ethyl-2-fluoro-5-methyl-8{2-(4-quinolinyloxy)ethyl}-6H-dipyrido[3,2-b:2',3'-e][1,4]diazepin-6-one Diethyl azodicarboxylate (DEAD) (14.3 mL, 91.0 mmol) was added drop-wise to a solution of 5,11-dihydro-11-ethyl-2-fluoro-8-(2-hydroxyethyl)-5-methyl-6H-dipyrido[3,2-b:2',3'-e][1,4]diazepin-6-one (19.2 g, 60.7 mmol), 4-hydroxyquinoline (13.2 g, 91.0 mmol) and Ph$_3$P (23.9 g, 91.0 mmol) in THF (300 mL) at room temperature. The mixture was stirred at room temperature for 1 h then was concentrated under reduced pressure. The residue was purified by flash chromatography (EtOAc:MeOH; 95:5) to give the title compound (17.9 g, 67% yield) as a white solid: MS (ESI) m/z 444 (M)$^+$.

Example V (Entry 1, Table 1)

2-Chloro-5,11-dihydro-11-ethyl-4-methyl-8-{2-(4-quinolinyloxy)ethyl}-6H-dipyrido[3,2-b:2',3'-e] [1,4]diazepin-6-one a) 2-Chloro-N-(2,6-dichlorofmethyl-3-pyridinyl)-3-pyridinecarboxamide NaHCO$_3$ (21.72 g, 258.6 mmol) was added to a solution of 3-amino-2,6-dichloro-4-methylpyridine (41.61 g, 235.1 mmol; prepared as described by K. G. Grozinger et al. J. Heterocyclic Chem. 1995, 32, 259–263) in MeCN (350 mL) and the resulting suspension was stirred for 15 min. A solution of 2-chloronicotinyl chloride (43.44 g, 246.8 mmol) in MeCN (500 mL) was then introduced over 30 min. The resulting suspension was stirred at room temperature. After 24 h, the solution was found to be acidic and so an additional amount of $NaHCO_3$ (3.00 g, 35.7 mmol) was added. The suspension was then stirred at room temperature for an additional 2 days. The mixture was then poured into a mixture of water (2 L) and ice (200 g) and stirred for 20 min. The solid was filtered and washed with water (500 mL) and the resulting solid was then dried over $P_2O_5$ under reduced pressure to give the title compound (62.55 g, 84% yield) as a white powder.

b) N-(2,6-dichlorofmethyl-3-pyridinyl)-2-(ethylamino)-3-pyridinecarboxamide

A solution of 2-chloro-N-(2,6-dichloro-4-methyl-3-pyridinyl)-3-pyridinecarboxamide (63.17 g, 194.0 mmol) and ethylamine (28.0 g, 583 mmol) in xylenes (250 mL) was stirred at 120 to 125° C. in a steel autoclave for 7 h. The resulting suspension was poured into water (1 L), stirred for 15 min and filtered. The residue was dissolved in EtOAc and washed with water (3×), brine and was dried over $MgSO_4$. The filtrate was extracted with EtOAc and the combined organic extracts were washed with water and brine and dried over $MgSO_4$. The two fractions were then combined and excess xylenes removed by co-distillation with benzene to give the title compound (61.98 g, pink solid) as the major component of a mixture of compounds. The material, not purified at this point, was used directly in the subsequent reaction.

c) 5-Bromo-N-(2,6-dichloro-4-methyl-3-pyridinyl)-2-(ethylamino)-3-pyridinecarboxamide Solid KOAc (22.2 g, 229 mmol) was added to a solution of crude N-(2,6-dichloro-4methyl-3-pyridinyl)-2-(ethylamino)-3-pyridinecarboxamide (61.98 g, <190 mmol) in AcOH (600 mL). A solution of $Br_2$ (9.7 mL, 191 mmol) was then added over 30 min. After stirring 30 min, additional amounts of KOAc and $Br_2$ were introduced until TLC indicated that no starting material remained (a total of 11.2 g of KOAc and 5.91 mL of $Br_2$). The solution was then poured into water (2 L) and stirred for 20 min. The solid was removed by filtration and then dissolved in $Et_2O$ (1 L). The ethereal solution was washed with water (3×), aqueous saturated $NaHCO_3$, brine then dried ($MgSO_4$) to give a mixture containing, as the major component, the title compound (77.7 g, yellow foam). The material was used directly in the subsequent reaction.

d) 8-Bromo-2-chloro-5,11-dihydro-11-ethyl-4-methyl-6H-dipyrido[3,2-b:2',3'-e][1,4]diazepin-6-one A solution of crude 5-bromo-N-(2,6-dichloro4-methyl-3-pyridinyl)-2-(ethylamino)-3-pyridinecarboxamide (77.7 g, mmol) in anhydrous pyridine (1.0 L) was heated to 50° C. A 1 M solution of NaHMDS in THF (418 mL, 418 mmol) was then added dropwise and stirring was continued for an additional 15 min. After cooling to room temperature, water (50 mL) was added and the mixture concentrated to two-thirds volume on a rotary evaporator. The residue was then poured into water (3 L). Filtration gave the title compound (23.44 g) as a tan solid. The filtrate was extracted with EtOAc (3×) and the combined extracts were washed with water and brine then dried ($NgSO_4$), filtered and concentrated under reduced pressure. The residue was purified by flash chromatography (hexane:EtOAc, 9:1 or $CHCl_3$) to give an additional amount of the title compound (14.06 g, for a total of 37.50 g, 50% yield for 3 steps).

e) 2-Chloro-5,11-dihydro-11-ethyl-4-methyl-8-(2-propenyl)-6H-dipyrido[3,2-b:2',3'-e][1,4]diazepin-6one A solution of 8-bromo-2-chloro-5,11-dihydro-11-ethyl-4-methyl-6H-dipyrido[3,2-b:2',3'-e][1,4]diazepin-6-one (12.6 g, 34.3 mmol) in DMF (25–0 mL) was degassed under reduced pressure for 20 min. $Pd(PPh_3)_4$ (775 mg, 0.7 mmol) was then added followed by allyltributyltin (12.5 mL, 41.1 mmol). After degassing under reduced pressure for 10 min, the mixture was heated to 100° C. for 7 h. The mixture was then concentrated under reduced pressure. The residue was purified by flash chromatography (hexane:EtOAc, 19:1) to give the title compound (8.04 g, 71% yield) as a yellow solid.

f) 2-Chloro-5,11-dihydro-11-ethyl-8-(2-hydroxyethyl)-4-methyl-6H-dipyrido[3,2-b:2',3'-e][1,4] diazepin-6-one A stream of $O_3$ was introduced into a cold (−78° C.) solution of 2-chloro-5,11-dihydro-11-ethyl-4-methyl-8-(2-propenyl)-6H-dipyrido[3,2-b:2',3'-e] [1,4]diazepin-6-one (8.04 g, 24.4 mmol) and Sudan III in $CH_2Cl_2$ (120 mL) and MeOH (120 mL). When the pink solution turned brown, $O_2$ was bubbled through the solution for 10 min. $NaBH_4$ (1.12 g, 29.4 mmol) was then added and the solution was allowed to warm to room temperature. After 30 min, an additional amount of $NaBH_4$ (500 mg) was added. After 1 h, aqueous saturated $NH_4Cl$ was then added and the mixture stirred for 20 min. The solution was concentrated under reduced pressure and extracted with $CH_2Cl_2$ (3×). The combined organic extracts were washed with brine, dried ($MgSO_4$), filtered and concentrated under reduced pressure. The residue was purified by flash chromatography ($CHCl_3$:EtOH, 97:3) to give the title compound (6.01 g, 74% yield) as a white solid.

g) 2-Chloro-5,11-dihydro-11-ethyl-4-methyl-8-{2-(4-quinolinyloxy)ethyl}-6H-dipyrido[3,2-b:2',3'-e] [1,4] diazepin-6-one Diethyl azodicarboxylate (DEAD) (83 µL, 0.53 mmol) was added drop-wise to a solution of 2-chloro-5,11-dihydro-11-ethyl-8-(2-hydroxyethyl)-4-methyl-6H-dipyrido[3,2-b:2',3'-e][1,4]diazepin-6-one (125 mg, 0.38 mmol), 4-hydroxyquinoline (76.3 mg, 0.53 mmol) and $Ph_3P$ (138 mg, 0.53 mmol) in THF (2.5 mL) at room temperature. The mixture was stirred at room temperature for 3 h then was concentrated under reduced pressure. The residue was dissolved in EtOAc (60 mL) and the solution was successively washed with 1 N aqueous NaOH (3×10 mL) and brine (15 mL) then was dried ($MgSO_4$), filtered and concentrated under reduced pressure. The residue was purified by flash chromatography (EtOAc:MeOH, 9:1) to give the title compound (52 mg, 30% yield) as a white solid: MS (ESI) m/z 460/462 $(MH)^+$.

Example VI (Entry 7, Table 1)

5,11-Dihydro-11-ethyl-2-fluoro4-methyl-8-{2-(4-quinolinyloxy)ethyl}-6H-dipytido[3,2-b:2',3'-e][1,4] diazepin-6-one a) 8-Bromo-5,11-dihydro-11-ethyl-2-{{(4-methoxyphenyl) methyl}amino}-4-methyl-6H-dipyrido[3,2-b:2',3'-e][1,4] diazepin-6-one 8-Bromo-2-chloro-5,11-dihydro-11-ethyl-4methyl-6H-dipyrido[3,2-b:2',3'-e] [1,4]diazepin-6-one (2.50 g, 6.80 mmol) was dissolved in dioxane (10 mL) in a glass pressure bottle and 4-methoxybenzylamine (4.0 mL, 30.6 mmol) was added to the solution. The mixture was heated to 170° C. for 5 days. The reaction mixture was cooled to room temperature and concentrated under reduced pressure. The residue was taken up in EtOAc and washed with 10% aqueous $NH_4Cl$, dried over $MgSO_4$, filtered and concentrated under reduced pressure to give a brown oil which was chromatographed over silica gel (hexane:EtOAC, 4:1). The title compound was obtained as a yellow solid (1.35 g, 42% yield).

b) 2-Amino-8-bromo-5,11-dihydro-11-ethyl-4methyl-6H-dipyrido[3,2-b:2',3'-e][1,4]diazepin-6-one 8-Bromo-5,11-dihydro-11-ethyl-2-{{(4-methoxyphenyl)methyl}amino}-4-methyl-6H-dipyrido[3,2-b:2',3'-e][1,4]diazepin-6-one (6.52 g, 18.7 mmol) was dissolved in trifluoroacetic acid (100 mL) and the solution was stirred magnetically at room temperature for 18 h. Trifluoroacetic acid was evaporated under reduced pressure and the residue was poured into a mixture containing water (450 mL), concentrated $NH_4OH$ (50 mL) and EtOAc (400 mL). The mixture was stirred magnetically for 2 h at room temperature. The organic phase was concentrated under reduced pressure.

The yellow precipitate was filtered off and washed with water, dried under reduced pressure to give 7.51 g of a yellow solid which was triturated in $Et_2O$ to give the title compound (5.12 g, 105% yield) as a yellow solid.

c) 8-Bromo-5,11-dihydro-11-ethyl-2-fluoro-4methyl-6H-dipyrido[3,2-b:2',3'-e][1,4]diazepin-6-one A plastic bottle was charged with 2-amino-8-bromo-5,11-dihydro-11-ethyl-4-methyl-6H-dipyrido[3,2-b:2',3'-e][1,4]diazepin-6-one (5.10 g, 14.6 mmol). HF-pyridine (100 g) was added and the resulting suspension was cooled to 0° C. Sodium nitrite (1.12 g, 16.1 mmol) was added in several portions over 30 min to produce a purple solution. The mixture was then stirred for 16 h at room temperature. The reaction mixture was poured onto ice and 6 N NaOH. The beige suspension was extracted with EtOAc. The organic extracts were combined, dried over $MgSO_4$, filtered and concentrated. The residue was triturated with $Et_2O$/hexane to give the title compound (4.30 g, 84% yield).

d) 5,11-Dihydro-11-ethyl-2-fluoro-4-methyl-8-(2-propenyl)-6H-dipyrido[3,2-b:2',3'-e][1,4]diazepin-6-one Allyltributyltin (7.77 mL, 25.1 mmol) and $Pd(Ph_3P)_4$ (1.32 g, 1.14 mmol) were added to a degassed ($N_2$ through solution for 30 min) solution of 8-bromo-5,11-dihydro-11-ethyl-2-fluoro-4-methyl-6H-dipyrido[3,2-b:2',3'-e][1,4]diazepin-6-one (8.0 g, 22.8 mmol) in DMF (114 mL). The mixture was heated to 90° C. for 3 h. The mixture was poured into water (250 mL) and extracted with EtOAc (4×250 mL). The combined organic layers were washed with 20% aqueous $NH_4OH$ (250 mL) and brine (250 mL), dried ($MgSO_4$), filtered and concentrated under reduced pressure. The residue was purified by flash chromatography (hexanes:EtOAc, 4:1 to 1:1) to give the title compound (3.16 g, 51% yield).

e) 5,11-Dihydro-11-ethyl-2-fluoro-8-(2-hydroxyethyl)methyl-6H-dipyrido[3,2-b:2',3'-e][1,4]diazepin-6-one A stream of ozonised oxygen was bubbled through a cold (−78° C.) solution of 5,11-dihydro-11-ethyl-2-fluoro-4-methyl-8-(2-propenyl)-6H-dipyrido[3,2-b:2',3'-e][1,4]diazepin-6-one (3.16 g, 10.1 mmol) in $CH_2Cl_2$ (25 mL) and MeOH (25 mL) for 45 min. A stream of $N_2$ was next bubbled through the solution for 15 min and then solid $NaBH_4$ (669 mg, 17.1 mmol) was added to the solution. The reaction mixture was allowed to warm to room temperature. After 2 h, aqueous saturated $NH_4Cl$ (50 mL) was added and the mixture was stirred at room temperature for 15 min. The organic solvents were removed under reduced pressure. The residual aqueous solution was extracted with $CHCl_3$ (3×100 mL). The combined organic layers were dried ($MgSO_4$), filtered and concentrated under reduced pressure. The residue was purified by flash chromatography (EtOAc:$CHCl_3$, 1:1) to give the title compound (2.40 g, 75% yield) as a white solid.

f) 5,11-Dihydro-11-ethyl-2-fluoromethyl-8-{2-(4-quinolinyloxy)ethyl}-6H-dipyrido[3,2-b:2',3'-e][1,4]diazepin-6-one Diisopropyl azodicarboxylate (DIAD) (117 µL, 0.59 mmol) was added drop-wise to a solution of 5,11-dihydro-11-ethyl-2-fluoro-8-(2-hydroxyethyl)4-methyl-6H-dipyrido[3,2-b:2',3'-e][1,4]diazepin-6-one (125 mg, 0.40 mmol), 4-hydroxyquinoline (86.0 mg, 0.59 mmol) and $Ph_3P$ (156 mg, 0.59 mmol) in THF (1.9 mL) at room temperature. The mixture was stirred at room temperature for 3 h then was concentrated under reduced pressure. The residue was dissolved in EtOAc (40 mL) and the solution was successively washed with 3 N aqueous NaOH (3×20 mL), aqueous saturated $NH_4Cl$ (15 mL), brine (15 mL) then was dried ($MgSO_4$), filtered and concentrated under reduced pressure. The residue was partially purified by flash chromatography (EtOAc:MeOH; 95:5). The solid was further purified by reverse phase HPLC (CombiPrep ADS-AQ 50×20 mm, 5 µ, 120 A, 5–100% MeCN+0.10% TFA/water+0.10% TFA in 25 min) to give the trifluoroacetic acid salt of the title compound (106 mg, 48% yield) as a white solid: MS (ESI) m/z 444 (MH)$^+$.

Example VII (Entry 5, Table 1)

11-(Cyclopropyl)-5,11-dihydro-2-fluoro-4-methyl-8-{2-(4-quinolinyloxy)-ethyl}-6H-dipytido[3,2-b:2',3'-e][1,4]diazepin-6-one a) 11-Cyclopropyl-5,11-dihydro-2-fluoro-8-(2-hydroxyethyl)-4methyl-6H-dipyrido[3,2-b:2',3'-e][1,4]diazepin-6-one The title compound was prepared from 8-bromo-2-chloro-11-cyclopropyl-5,11-dihydro-4-methyl-6H-dipyrido[3,2-b:2',3'-e][1,4]diazepin-6-one using a procedure similar to that of the corresponding 11-ethyl analog described in example VI.

b) 11-Cyclopropyl-5,11-dihydro-2-fluoro-4-methyl-8-{2-(4-quinolinyloxy)ethyl-}6H-dipyrido[3,2-b:2',3'-e][1,4]diazepin-6-one Diisopropyl azodicarboxylate (DIAD) (131 µL, 0.66 mmol) was added drop-wise to a solution of 11-(cyclopropyl)-5,11-dihydro-2-fluoro-8-(2-hydroxyethyl)-4methyl-6H-dipyrido[3,2-b:2',3'-e] [1,4]diazepin-6-one (140 mg, 0.44 mmol), 4-hydroxyquinoline (96.4 mg, 0.66 mmol) and $Ph_3P$ (124 mg, 0.66 mmol) in THF (2.2 mL) at room temperature. The mixture was stirred at room temperature for 3 h then was concentrated under reduced pressure. The residue was dissolved in EtOAc (60 mL) and the solution was successively washed with 3 N aqueous NaOH (3×20 mL), aqueous saturated $NH_4Cl$ (20 mL) and brine (20 mL) then was dried ($MgSO_4$), filtered and concentrated under reduced pressure. The residue was partially purified by flash chromatography (EtOAc:MeOH; 95:5). The solid was further purified by reverse phase HPLC (CombiPrep ADS-AQ 50×20 mm, 5 µ120 A, 5–100% MeCN+0.10% TFA/water+0.10% TFA in 25 min) to give the bifluoroacetic acid salt of the title compound (104 mg, 43% yield) as a white solid: MS (ESI) m/z 456 (MH)$^+$.

Example VIII (Entry 8, Table 1)

5,11-Dihydro-11-ethyl-4-methyl-8-{2-(4-quinolinyloxy)ethyl}-6H-dipyrido[3,2-b:2',3'-e][1,4]diazepin-6-one a) 5,11-Dihydro-11-ethyl-8-(2-hydroxyethyl)-4-methyl-6H-dipyido[3,2-b:2',3'-e][1,4]diazepin-6-one A mixture of 2-chloro-5,11-dihydro-11-ethyl-8-(2-hydroxyethyl)-4-methyl-6H-dipyrido[3,2-b:2',3'-e][1,4]

diazepin-6-one(168 mg, 0.51 mmol), ammonium formate (318 mg, 5.1 mmol) and 10% Pd/C (50 mg) in ETOH (6 mL) was stirred at room temperature. After 24 h, additional amounts of ammonium formate (200 mg, mmol) and 10% Pd/C (50 mg) were added. After stirring an additional 24 h, the reaction was concentrated under reduced pressure. The residue was dissolved in CHCl₃ and the mixture was washed with aqueous saturated NaHCO₃, dried (MgSO₄), filtered and concentrated under reduced pressure to give the title compound (122 mg, 81%) as a yellow oil.

b) 5,11-Dihydro-11-ethyl-4-methyl-8-{2-(4-quinolinyloxy) ethyl}-6H-dipyrido[3,2-b:2',3'-e][1,4]diazepin-6-one Diisopropyl azodicarboxylate (DIAD) (42 μL, 0.21 mmol) was added drop-wise to a solution of 5,11-dihydro-11-ethyl-8-(2-hydroxyethyl)-4-methyl-6H-dipyrido[3,2-b:2',3'-e][1,4]diazepin-6-one (42.0 mg, 0.14 mmol), 4-hydroxyquinoline (31 mg, 0.21 mmol) and Ph₃P (55.4 mg, 0.21 mmol) in THF (0.7 mL) at room temperature. The mixture was stirred at room temperature for 2 h then was concentrated under reduced pressure. The residue was dissolved in EtOAc (60 mL) and the solution was successively washed with 3 N aqueous NaOH (3×20 mL), aqueous saturated NH₄Cl (20 mL) and brine (20 mL) then was dried (MgSO₄), filtered and concentrated under reduced pressure. The residue was partially purified by flash chromatography (EtOAc:MeOH; 95:5). The solid was further purified by reverse phase HPLC (CombiPrep ADS-AQ 50×20 mm, 5 μ, 120 A, 5–100% MeCN+0.10% TFA/water+0.10% TFA in 25 min) to give the trifluoroacetic acid salt of the title compound (14.2 mg, 19% yield) as a white solid: MS (ESI) m/z 426 (MH)⁺.

Example IX (Entry 3, Table 1)

11-(Cyclopropyl)-5,11-dihydro-4-methyl-8-{2-(4-quinolinyloxy)ethyl}-6H-dipyrido[3,2-b:2',3'-e] [1, 4]diazepin-6-one a) 5-Bromo-2-chloro-N-(2,6dichloro-4-methyl-3-pyridinyl)-3-pyridinecarboxamide 3-Amino-2,6-dichloro-4-methylpyridine (0.51 g, 2.85 mmol) was dissolved in toluene (35 mL) and pyridine (0.27 mL, 3.28 mmol) was added. 5-Bromo-2-chloro-3-pyridinecarbonyl chloride (0.80 g, 3.14 mmol) was then added dropwise over 30 min. The resulting mixture was stirred at room temperature for 1 h, diluted with water and extracted with toluene (2×). The combined organic extracts were dried (MgSO₄), filtered and concentrated under reduced pressure. The resulting thick oil was triturated with CH₂Cl₂, and the white solid collected via suction filtration to give the title compound (0.41 g, 36% yield).

b) 5-Bromo-2-(cyclopropylamino)-N-(2,6-dichloro-4-methyl-3-pyridinyl)-3-pyridinecarboxamide A solution of 5-bromo-2-chloro-N-(2,6-dichloro-4-methyl-3-pyridinyl)-3-pyridinecarboxamide (3.00 g, 7.61 mmol) and cyclopropylamine (2.11 mL, 30.5 mmol) in xylenes was heated in a sealed tube at 120° C. for 24 h. The reaction was cooled to 0° C., diluted with water and extracted with EtOAc (2×). The combined organic extracts were dried (MgSO₄), filtered and concentrated under reduced pressure. The resulting residue was purified by trituration (Et₂O:hexane, 3:1) to give the title compound (2.35 g, 75% yield) as a pale yellow solid.

c) 8-Bromo-2-chloro-11-cyclopropyl-5,11-dihydro4methyl-6H-dipyrido[3,2-b:2',3'-e][1,4]diazepin-6-one A solution of 5-bromo-2-(cyclopropylamino)-N-(2,6-dichloro-4-methyl-3-pyridinyl)-3-pyridinecarboxamide (105 mg, 0.254 mmol) in pyridine (3.0 mL) was heated to 50° C. while a 1 M solution of NaHMDS in THF (0.53 mL, 0.53 mmol) was added. The resulting solution was stirred at 50° C. for 3 h. The reaction was quenched with aqueous saturated NH₄Cl, diluted with water and extracted with EtOAc (3×). The combined organic extracts were washed with brine, dried (MgSO₄), filtered and concentrated under reduced pressure. The resulting residue was purified via flash chromatography (hexane:EtOAc, 7:3) to give the title compound (32 mg, 33% yield).

d) 2-Chloro-11-cyclopropyl-5,11-dihydrofmethyl-8-(2-propenyl)-6H-dipyrido[3,2-b:2',3'-e][1,4]diazepin-6-one A solution of 8-bromo-2-chloro-11-cyclopropyl-5,11-dihydro-4-methyl-6H-dipyrido[3,2-b:2',3'-e][1,4]diazepin-6-one (0.046 g, 0.122 mmol) in DMF (2.0 mL) was degassed by sparging with N₂ for 10 min. Pd(PPh₃)₄ (2.8 mg, 0.003 mmol) and allyltributyltin (0.45 mL, 0.146 mmol) were added and the resulting solution was heated to 90° C. for 2.5 h. The reaction mixture was diluted with water and extracted with CH₂Cl₂ (3×) and EtOAc (2×). The combined organic extracts were dried (MgSO₄), filtered and concentrated under reduced pressure. The resulting residue was purified via flash chromatography (hexane to hexane:EtOAc, 7:3) to give the title compound (0.033 g, 80% yield).

e) 2-Chloro-41-cyclopropyl-5,11-dihydro-8-(2-hydroxyethyl)methyl-6H-dipyrido[3,2-b:2',3'-e][1,4]diazepin-6-one A cold (−78° C.) solution of 2-chloro-11-cyclopropyl-5,11-dihydro-4methyl-8-(2-propenyl)-6H-dipyrido[3,2-b:2',3'-e] [1,4]diazepin-6-one (0.82 g, 2.43 mmol) in CH₂Cl₂ (7.5 mL) and MeOH (7.5 mL) was saturated with O₃ until the solution turned pale blue. The reaction mixture was left at −78° C. for 10 min, then NaBH₄ (0.23 g, 9.71 mmol) was added and the mixture was allowed to warm slowly to room temperature over 2 h. The reaction was quenched with aqueous 10% citric acid solution and extracted with EtOAc (3×). The organic extracts were combined, washed with brine, dried (MgSO₄), filtered and concentrated under reduced pressure. The resulting residue was purified via flash chromatography (MeOH:CH₂C₂, 2 to 10%) to give the title compound (0.41 g, 60% yield) as a white solid.

f) 11-Cyclopropyl-5,11-dihydro-8-(2-hydroxyethyl)methyl-6H-dipyrido[3,2-b:2',3'-e][1,4]diazepin-6-one The title compound was prepared using a method similar to that described for the 11-ethyl analog in example VIIIa.

g) 11-Cyclopropyl-5,11-dihydro-4-methyl-8-{2-(4-quinolinyloxy)ethyl}-6H-dipyrido[3,2-b:2',3'-e][1,4] diazepin-6-one Diisopropyl azodicarboxylate (DIAD) (167 μL, 0.85 mmol) was added drop-wise to a solution of 11-(cyclopropyl)-5,11-dihydro-8-(2-hydroxyethyl)-4-methyl-6H-dipyrido[3,2-b:2',3'-e][1,4]diazepin-6-one (175 mg, 0.57 mmol), 4-hydroxyquinoline (123 mg, 0.85 mmol) and Ph₃P (223 mg, 0.85 mmol) in THF (2.8 mL) at room temperature. The mixture was stirred at room temperature for 3 h then was concentrated under reduced pressure. The residue was dissolved in EtOAc (60 mL) and the solution was successively washed with 3 N aqueous NaOH (3×20 mL), aqueous saturated NH₄Cl (20 mL) and brine (20 mL) then was dried (MgSO₄), filtered and concentrated under reduced pressure. The residue was purified by flash chromatography (EtOAc:MeOH; 95:5) to give the title compound (74 mg, 30% yield) as a white solid: MS (ESI) m/z 438 (MH)⁺.

Example X (Entry 21, Table 1)

5,11-Dihydro-11-ethyl-5-methyl-8-{2-{(1-oxido-4-quinolinyl)oxy}ethyl}-6H-dipytido[3,2-b:2',3'-e][1, 4]diazepin-6-one Solid mCPBA (80–85%, m-chloroperbenzoic acid) (2.21 g, 10.2 mmol) was added to a solution of 5,11-dihydro-11- ethyl-5-methyl-8-{2-(4-quinolinyloxy)ethyl}-6H-dipyrido [3,2-b:2',3'-e][1,4]diazepin-6-one (2.56 g, 6.02 mmol) in CH$_2$Cl$_2$ (30 mL) and THF (30 mL) at room temperature (note that the reaction can be performed in CH$_2$Cl$_2$ alone). The mixture was stirred at room temperature for 1 h then was concentrated under reduced pressure. The residue was dissolved in CHCl$_3$ (400 mL), the solution was successively washed with aqueous 10% Na$_2$S$_2$O$_3$ (3×75 mL), aqueous saturated NaHCO$_3$ (3×75 mL) and brine (75 mL), dried (MgSO$_4$), filtered and concentrated under reduced pressure. The residue was purified by flash chromatography (CHCl$_3$:MeOH, 9:1) to give the title compound (2.01 g, 76% yield) as a white solid: MS (ESI) m/z 442 (MH)$^+$.

Example XI (Entry 17, Table 1)

2-Chloro-5,11-dihydro-11-ethyl-5-methyl-8-{2-{(1-oxido-4-quinolinyl)oxy}-ethyl}-6H-dipyrido[3,2-b:2',3'-e][1,4]diazepin-6-one Using a procedure identical to that of example X, 2-chloro-5,11-dihydro-11-ethyl-5-methyl-8-{2-(4-quinolinyloxy)ethyl}-6H-dipyrido[3,2-b:2',3'-e] [1,4] diazepin-6-one (2.70 g, 5.87 mmol) gave the title compound (2.05 g, 73% yield) as a white solid: MS (ESI) m/z 476/478 (MH)$^+$.

Example XII (Entry 11, Table 1)

5,11-Dihydro-11-ethyl-2-fluoro-5-methyl-8-{2-{(1-oxido-4-quinolinyl)oxy}-ethyl}-6H-dipyrido[3,2-b:2',3'-e] [1,4]diazepin-6-one Solid mCPBA (457 mg, 2.12 mmol) was added to a solution of 5,11-dihydro-2-fluoro-11-ethyl-5-methyl-8-{2-(4-quinolinyloxy)ethyl}-6H-dipyrido[3,2-b:2',3'-e][1,4] diazepin-6-one (470 mg, 1.06 mmol) in CH$_2$Cl$_2$ (10 mL). The mixture was stirred at room temperature for 13 h then was concentrated under reduced pressure. The residue was dissolved in CHCl$_3$ (75 mL), the solution was successively washed with aqueous 10% Na$_2$S$_2$O$_3$ (3×25 mL), aqueous saturated NaHCO$_3$ (3×25 mL) and brine (25 mL), dried (MgSO$_4$), filtered and concentrated under reduced pressure. The residue was purified by flash chromatography (CHCl$_3$:MeOH, 19:1 to 9:1) to give the title compound (250 mg, 51% yield) as a white solid: MS (ESI) m/z 460 (MH)$^+$.

Example XIII (Entry 10, Table 1)

2-Chloro-11-cyclopropyl-5,11-dihydro-5-methyl-8-{2-{(1-oxido-4-quinolinyl)oxy}ethyl}-6H-dipyrido [3,2-b:2',3'-e] [1,4]diazepin-6-one Solid mCPBA (177 mg, 0.82 mmol) was added to a solution of 2-chloro-11-cyclopropyl-5,11-dihydro-5-methyl-8-{2-(4-quinolinyloxy)ethyl}-6H-dipyrido[3,2-b:2',3'-e][1,4]diazepin-6-one (143 mg, 0.30 mmol) in CH$_2$Cl$_2$ (3 mL) and THF (3 mL). The mixture was stirred at room temperature for 14 h then was concentrated under reduced pressure. The residue was dissolved in EtOAc (50 mL), the solution was successively washed with aqueous 10% Na$_2$S$_2$O$_3$ (3×10 mL), aqueous saturated NaHCO$_3$ (3×10 mL) and brine (10 mL), dried (MgSO$_4$), filtered and concentrated under reduced pressure. The residue was partially purified by flash chromatography (EtOAc:MeOH, 95:5 to CH$_2$Cl$_2$:MeOH, 9:1). The impure compound was further purified by reverse phase HPLC (CombiPrep ADS-AQ 50×20 mm, 5 μ, 120 A, 5–100% MeCN+0.10% TFA/water+ 0.10% TFA in 25 min). The pure fractions were treated with aqueous saturated NaHCO$_3$, extracted with EtOAc and the solution was dried (MgSO$_4$), filtered and concentrated under reduced pressure to give the title compound (28.3 mg, 19%) as a white solid: MS (ESI) m/z 488/490 (MH)$^+$.

Example XIV (Entry 14, Table 1)

2-Chloro-5,11-dihydro-11-ethyl-4-methyl-8-{2-{(1-oxido-4-quinolinyl)-oxy}ethyl}-6H-dipyrido[3,2-b:2',3'-e][1,4]diazepin-6-one Solid mCPBA (46.9 mg, 0.22 mmol) was added to a solution of 2-chloro-5,11-dihydro-11-ethyl-5-methyl-8-{2-(4-quinolinyloxy)ethyl}-6H-dipyrido [3,2-b:2',3'-e][1,4] diazepin-6-one (50.0 mg, 0.11 mmol) in CH$_2$Cl$_2$ (2.2 mL). The mixture was stirred at room temperature for 1 h then was concentrated under reduced pressure. The residue was dissolved in EtOAc (50 mL), the solution was successively washed with aqueous 10% Na$_2$S$_2$O$_3$ (3×10 mL), aqueous saturated NaHCO$_3$ (3×10 mL) and brine (10 mL), dried (MgSO$_4$), filtered and concentrated under reduced pressure. The residue was purified by reverse phase HPLC (CombiPrep ADS-AQ 50×20 mm, 5 μ, 120 A, 5–100% MeCN+0.10% TFA/water+0.10% TFA in 25 min). The pure fractions were treated with aqueous saturated NaHCO$_3$, extracted with EtOAc and the solution was dried (MgSO$_4$), filtered and concentrated under reduced pressure to give the title compound (32.5 mg, 63%) as a white solid: MS (ESI) m/z 488/490 (MH)$^+$.

Example XV (Entry 9, Table 1)

5,11-Dihydro-11-ethyl-2-fluoro-4-methyl-8-{2-{(1-oxido-4-quinolinyl)-oxy}ethy}-6H-dipyrido[3,2-b:2', 3'-e][1,4]diazepin-6-one Using a procedure similar to that of example XIV, 5,11-dihydro-11-ethyl-2-fluoro-4-methyl-8-{2-(4-quinolinyloxy) ethyl}-6H-dipyrido[3,2-b:2',3'-e] [1,4]diazepin-6-one (125 mg, 0.28 mmol) gave the title compound (40 mg, 31%) as a white solid: MS (ESI) m/z 460 (MH)$^+$.

Example XVI (Entry 12, Table 1)

5,11-Dihydro-11-ethyl-4-methyl-8-{2-{(1-oxido-4-quinolinyl)oxy}ethyl}-6H-dipyrido[3,2-b:2',3'-e][1, 4]diazepin-6-one Solid mCPBA (163 mg, 0.75 mmol) was added to a solution of 5,11-dihydro-11-ethyl-4-methyl-8-{2-(4-quinolinyloxy)ethyl}-6H-dipyrido[3,2-b:2',3'-e] [1,4] diazepin-6-one (144 mg, 0.34 mmol) in CH$_2$Cl$_2$ (7.5 mL). The solution was stirred at room temperature for 2 h. The mixture was diluted with CH$_2$Cl$_2$ (125 mL), washed successively with aqueous 10% Na$_2$S$_2$O$_3$ (2×25 mL), aqueous saturated NaHCO$_3$ (2×25 mL) and brine (25 mL), then was dried (MgSO$_4$), filtered and concentrated under reduced pressure. The residue was purified by flash chromatography (CH$_2$Cl$_2$:MeOH, 10:1) to give the title compound (102 mg, 68% yield) as a white solid: MS (ESI) m/z 442 (MH)$^+$.

Example XVII (Entry 15, Table 1)

11-Cyclopropyl-5,11-dihydro-11-ethyl-4-methyl-8-
{2-{(1-oxido-4-quinolinyl)oxy}ethyl}-6H-dipyrido
[3,2-b:2',3'-e] [1,4]diazepin-6-one Using a procedure similar to that of example XIV, 11-cyclopropyl-5,11-dihydro-11-4-methyl-8-{2-(4-quinolinyloxy)ethyl}-6H-dipyrido[3,2-b:2',3'-e] [1,4]diazepin-6-one (37.1 mg, 0.085 mmol) gave the title compound (35 mg, 91%) as a white solid: MS (ESI) m/z 454 (MH)$^+$.

Example XVIII (Entry 25, Table 1)

2-Chloro-5,11-dihydro-11-ethyl-4-methyl-8-{2-(5-quinolinyloxy)ethyl}-6H-dipyrido[3,2-b:2',3'-e][1,4]diazepin-6-one Diethyl azodicarboxylate (DEAD) (77 µL, 0.49 mmol) was added drop wise to a solution of 2-chloro-5,11-dihydro-11-ethyl-8-(2-hydroxyethyl)4methyl-6H-dipyrido[3,2-b:2',3'-e][1,4]diazepin-6-one (125 mg, 0.38 mmol), 5-hydroxyquinoline (70.9 mg, 0.49 mmol) and Ph$_3$P (128 mg, 0.49 mmol) in THF (2.5 mL) at room temperature. After 1.5 h, additional amounts of DEAD (35 µL, 0.22 mmol) and PPh$_3$ (59 mg, 0.22 mmol) were added to the mixture. The mixture was stirred at room temperature for 1 h then was diluted in EtOAc (50 mL) and the solution was successively washed with aqueous 1 N NaOH (4×10 mL) and brine (15 mL) then was dried (MgSO$_4$), filtered and concentrated under reduced pressure. The residue was purified by flash chromatography (CH$_2$Cl$_2$:acetone, 85:15). The resulting solid was triturated with Et$_2$O to give the title compound (38 mg, 22% yield) as a white solid: MS (ESI) m/z 460/462 (MH)$^+$.

Example XIX (Entry 20, Table 1)

2-Chloro-5,11-dihydro-11-ethyl-5-methyl-8-{2-{(1-oxido-5-quinolinyl)-oxy}ethyl}-6H-dipyrido[3,2-b:2',3'-e] [1,4]diazepin-6-one Diethyl azodicarboxylate (DEAD) (160 µL, 1.01 mmol) was added drop-wise to a solution of 2-chloro-5,11-dihydro-11-ethyl-8-(2-hydroxyethyl)-5-methyl-6H-dipyrido[3,2-b:2',3'-e][1,4]diazepin-6-one (225 mg, 0.68 mmol), 5-hydroxyquinoline (147 mg, 1.01 mmol) and Ph$_3$P (266 mg, 1.01 mmol) in THF (3.4 mL) at room temperature. The mixture was stirred at room temperature for 3 h then was concentrated under reduced pressure. The residue was partially purified by flash chromatography (EtOAc:MeOH; 95:5). The fractions containing the 5-quinolinyloxy derivative were concentrated, dissolved in CH$_2$Cl$_2$ (2 mL) and THF (5 mL) and treated with mCPBA (80%, 248 mg, 1.15 mmol) at room temperature. The solution was stirred at room temperature for 2.5 h, then was concentrated under reduced pressure. The residue was dissolved in EtOAc (50 mL), washed successively with aqueous 10% Na$_2$S$_2$O$_3$ (3×10 mL), aqueous saturated NaHCO$_3$ (3×10 mL) and brine (10 mL), then was dried (MgSO$_4$), filtered and concentrated under reduced pressure. The residue was purified by flash chromatography (EtOAc:MeOH, 95:5 to CH$_2$Cl$_2$:MeOH, 9:1) to give the title compound (113 mg, 35% yield for 2 steps) as a white solid: MS (ESI) m/z 476/478 (MH)$^+$.

Example XX (Entry 18, Table 1)

5,11-Dihydro-11-ethyl-2-fluoro-5-methyl-8-{2-{(1-oxido-5-quinolinyl)-oxy}ethyl}-6H-dipyrido[3,2-b:2',3'-e][1,4]diazepin-6-one Using a procedure identical to that of example XIX, 5,11-dihydro-11-ethyl-2-fluoro-8-(2-hydroxyethyl)-5-methyl-6H-dipyrido[3,2-b: 2',3'-e][1,4]diazepin-6-one (267 mg, 0.84 mmol) gave the title compound (204 mg, 52% yield for 2 steps) as a white solid: MS (ESI) m/z 460 (MH)$^+$.

Example XXI (Entry 19, Table 1)

2-Chloro-5,11-dihydro-11-ethyl-4-methyl-8-{2-{(1-oxido-5-quinolinyl)-oxy}ethyl}-6H-dipyrido[3,2-b:2',3'-e][1,4]diazepin-6-one Using a procedure similar to that of example XIX but using diisopropyl azodicarboxylate (DIAD) instead of diethyl azodicarboxylate, 2-chloro-5,11-dihydro-11-ethyl-8-(2-hydroxyethyl)-4-methyl-6H-dipyrido[3,2-b:2',3'-e] [1,4]diazepin-6-one (223 mg, 0.67 mmol) gave the title compound (43.4 mg, 14% yield for 2 steps) as a white solid: MS (ESI) m/z 476/478 (MH)$^+$.

Example XXII (Entry 23, Table 1)

5,11-Dihydro-11-ethyl-2-fluoro-4-methyl-8-{2-{(1-oxido-5-quinolinyl)-oxy}ethyl}-6H-dipyrido[3,2-b:2',3'-e][1,4]diazepin-6-one Using a procedure similar to that of example XXI, 5,11-dihydro-11-ethyl-2-fluoro-8-(2-hydroxyethyl)-4-methyl-6H-dipyrido[3,2-b:2',3'-e] [1,4]diazepin-6-one (250 mg, 0.79 mmol) gave the title compound (64.7 mg, 18% yield for 2 steps) as a white solid: MS (ESI) m/z 460 (MH)$^+$.

Example XXIII

Entry 22, Table 1

2-Chloro-5,11-dihydro-11-ethyl-8-{2-{(1-oxido-4-quinolinyl)oxy}ethyl}-6H-dipyrido[3,2-b:2',3'-e][1, 4]diazepin-6-one MS (ESI) m/z 462/464 (MH)$^+$.

Example XXIV

Entry 26, Table 1

5,11-Dihydro-5,11-diethyl-8-{2-(4-quinolinyloxy) ethyl}-6H-dipyrido[3,2-b:2',3'-e][4]diazepin-6-one MS (ESI) m/z 440 (MH)$^+$.

Example XXV

Entry 27, Table 1

5,11-Dihydro-5,11-diethyl-8-{2-{(1-oxido-4-quinolinyl)oxy}ethyl}-6H-dipyrtido[3,2-b:2;3'-e][1, 4]diazepin-6-one MS (ESI) m/z 456 (MH)$^+$.

Example XXVI (Entry 28, Table 1)

2,5-Dimethyl-5,11-dihydro-11-ethyl-8-{2-{(1-oxido-4-quinolinyl)oxy}ethyl}-6H-dipyrido[3,2-b:2',3'-e] [1,4]diazepin-6-one a) 5-Bromo-2-chloro-N-(6-chloro-2-methyl-3-pyridinyl)-3-pyridinecarboxamide NaHCO$_3$ (3.9 g, 46.4 mmol) was added to a solution of 3-amino-2-chloro-6- methylpyridine (2.2 g, 15.4 mmol;

prepared as described by K. G. Grozinger et al. J. Heterocyclic Chem. 1995,32,259–263) in MeCN (50 mL). The resulting suspension was stirred for 15 min. and a solution of crude 5-bromo-2-chloro-3-pyridinecarbonyl chloride (prepared from 5-bromo-2-hydroxy-3-pyridinecarboxylic acid and SOCl$_2$ [as described by T. W. Gero et al. in Synth. Commun. 1989, 19, 553–559 (incorporated herein by reference) but with omission of the aqueous work-up] (4 g,) in MeCN (10 mL) was introduced over 30 min. The resulting suspension was stirred at room temperature. After 24 h, the mixture was poured into a mixture of water (100 mL) and ice (10 g) and stirred for 20 min. The suspension was filtered and the resulting solid was washed with water (50 mL) and hexane (25 mL), then dried over P$_2$O$_5$ under reduced pressure to give the title compound (1.8 g, 31% yield) as a white powder.

b) 5-Bromo-N-(2-chloro-6-methyl-3-pyridinyl)-2-(ethylamino)-3-pyridinecarboxamide A solution of 5-bromo-2-chloro-N-(2-chloro-6-methyl-3-pyridinyl)-3-pyridinecarboxamide (1.7 g, 4.8 mmol) and ethylamine (2M in THF, 10.5 mmol, 5.2 mL) in THF (5 mL) was stirred at 90 to 95° C. in a steel autoclave for 16 h. The resulting mixture was poured into water (100 mL), stirred for 15 min and filtered. The solid was washed with water followed by hexane to give the title compound as a yellow solid (1.58 g, 89% yield).

c) 8Bromo-5,11-dihydro-2–5-dimethyl-11-ethyl-6H-dipyrido[3,2-b:2',3'-e][1,4]diazepin-6-one A solution of crude 5-bromo-N-(2-dichloro-6-methyl-3-pyridinyl)-2-(ethylamino)-3-pyridinecarboxamide (0.7 g, 1.8 mmol) in anhydrous pyridine (18 mL) was heated to 50° C. A 1 M solution of NaHMDS in THF (7.2 mL, 7.2 mmol) was then added dropwise and stirring was continued for an additional 3h. After cooling to room temperature, methyl iodide (0.6 mL, 9 mmol) was added and the reaction was stirred overnight. Water (25 mL) was added and the mixture was extracted with EtOAc (3×) and the combined extracts were washed with water and brine then dried (MgSO$_4$), filtered and concentrated under reduced pressure. The residue was purified by flash chromatography (hexane:EtOAc, 8:2) to give the title compound (259 mg, 41% yield).

d) 5,11-Dihydro-2,5-dimethyl-11-ethyl-8-(2-propenyl)-6H-dipyrido[3,2-b:2',3'-e][1,4]diazepin-6-one A solution of 8-bromo-5,11-dihydro-2,5-dimethyl-11-ethyl-6H-dipyrido[3,2-b:2',3'-e][1,4]diazepin-6-one (258 mg, 0.7 mmol) in DMF (7.4 mL) was degassed under reduced pressure for 20 min. Pd(PPh$_3$)$_4$ (43 mg, 0.04 mmol) was then added followed by allyltributyltin (0.3 mL, 0.85 mmol). After degassing under reduced pressure for 10 min, the mixture was heated to 100° C. for 1.5 h. The mixture was then concentrated under reduced pressure. The residue was purified by flash chromatography (hexane:EtOAc, 8:2) to give the title compound (184 mg, 98% yield) as a yellow solid.

e) 5,11-Dihydro-2,5-dimethyl-11-ethyl-8-(2-hydroxyethyl)-6H-dipyrido[3,2-b:2',3'-e][1,4]diazepin-6-one A stream of O$_3$ was introduced into a cold (−78° C.) solution of 5,11-dihydro-2,5-dimethyl-11-ethyl-8-(2-propenyl)-6H-dipyrido[3,2-b:2',3'-e][1,4]diazepin-6-one (187 mg, 0.6 mmol) and Sudan III in CH$_2$Cl$_2$ (3 mL) and MeOH (3 mL). When the pink solution turned brown, O$_2$ was bubbled through the solution for 10 min. NaBH$_4$ (57 mg, 1.52 mmol) was then added and the solution was allowed to warm to room temperature. After 30 min, an additional amount of NaBH$_4$ (20 mg) was added. After 2 h, aqueous saturated NH$_4$Cl was then added and the mixture stirred for 20 min. The solution was concentrated if under reduced pressure and extracted with CH$_2$Cl$_2$ (3×). The combined organic extracts were washed with brine, dried (MgSO$_4$), filtered and concentrated under reduced pressure. The residue was purified by flash chromatography (EtOAc:Hexane 6:4) to give the title compound (111 mg, 58% yield) as a white solid.

f) 2,5-Dimethyl-5,11-dihydro-11-ethyl-8-{2-(4-quinolinyloxy)ethyl}-6H-dipyrido[3,2-b:2',3'-e] [1,4]diazepin-6-one Diethyl azodicarboxylate (DEAD) (139 µL, 0.88 mmol) was added dropwise to a solution of 5,11-dihydro-2,5-dimethyl-11-ethyl-8-(2-hydroxyethyl)-6H-dipyrido[3,2-b:2',3'-e] [1,4]diazepin-6-one (110 mg, 0.35 mmol), 4-hydroxyquinoline (128 mg, 0.88 mmol) and Ph$_3$P (231 mg, 0.88 mmol) in THF (3.5 mL) at room temperature. The mixture was stirred at room temperature for 16 h. The reaction mixture was diluted in EtOAc (60 mL) and the solution was successively washed with 1 N aqueous NaOH (3×10 mL) and brine (15 mL) then was dried (MgSO$_4$), filtered and concentrated under reduced pressure. The residue was purified by flash chromatography (EtOAc then EtOAc:MeOH, 9.5:0.5) to give the title compound (57 mg, 37% yield) as a white solid: MS (ESI) m/z 440 (MH)$^+$.

g) 5,11-Dihydro-2,5-dimethyl-11-ethyl-8-{2-{(1-oxido-4-quinolinyl)oxy}ethyl}-6H-dipyrido[3,2-b:2',3'-e] [1,4]diazepin-6-one Solid mCPBA (80–85%, m-chloroperbenzoic acid) (60 mg, 0.28 mmol) was added to a solution of 5,11-dihydro-2,5-dimethyl-11-ethyl-8-{2-(4-quinolinyloxy)ethyl}-6H-dipyrido[3,2-b:2',3'-e] [1,4]diazepin-6-one (55 mg, 0.13 mmol) in CH$_2$Cl$_2$ (1.3 mL) at room temperature. The mixture was stirred at room temperature for 2.5 h then diluted with CH$_2$Cl$_2$. The resulting solution was successively washed with aqueous 10% Na$_2$S$_2$O$_3$, aqueous saturated NaHCO$_3$ and brine, dried (MgSO$_4$), filtered and concentrated under reduced pressure. The residue was purified by flash chromatography (MeOH/EtOAc,2% to 5%) to give the title compound (59 mg, 99% yield) as a white solid: MS (ES) m/z 456 (MH)$^+$.

Example XXVII (Entry 29, Table 1)

5,11-Dihydro-11-ethyl-5-methyl-8-{2-{(1-oxido- 4-quinolinyl)oxy}ethyl}-2-(trifluoromethyl)-6H-dipyrido[3,2-b:2',3'-e] [1,4]diazepin-6-one a) 2-(Ethylamino)-3nitro-6-(trifluoromethyl)pyridine To a solution of 2-nitroacetamide ammonium salt (4 g, 33 mmol) in water (165 mL) was added piperidinium acetate (33 mmol) in water followed by slow addition of 4-ethoxy-1,1,1-trifluoro-3-buten-2-one (6.1 mL, 43 mmol) in MeOH (11 mL). The reaction was stirred for 2 h at room temperature and at reflux for 3 h. The reaction mixture was allowed to cool to 45° C. and aqueous HCl (1N) was added until the pH was acidic. After 1 h at room temperature, the reaction mixture was extracted with CH$_2$Cl$_2$ (3×). The combined organic layer was successively washed with water and brine, dried (MgSO$_4$), filtered and concentrated under reduced pressure. The residue was purified by flash chromatography (EtOAc, then EtOAC:MeOH, 9:1) to give 3-nitro-6-(trifluoromethyl)-2(1H)-pyridinone (2.7 g, 40% yield) as a yellow solid.

To a solution of 3-nitro-6-(trifluoromethyl)-2(1H)-pyridinone (2.4 g, 11.5 mmol) in DMF (69 mL) was added sodium hydride (350 mg, 13.8 mmol). The reaction was stirred for 30 min at 45° C., cooled to room temperature and N-phenyltrifluromethanesulfonimide (4.9 g, 13.8 mmol) was added. After 1 h, a 2 M solution of ethylamine in THF (13 mL, 25 mmol) was added. The reaction was stirred at room temperature overnight. The reaction mixture was poured into water (100 mL) and extracted with EtOAc (3×). The combined organic layer was successively washed water and brine, dried (MgSO$_4$), filtered and concentrated under reduced pressure. The residue was purified by flash chromatography (hexane:EtOAc, 9:1) to give the desired compound (1.1 g, 41% yield) as a yellow oil.

b) 3-Amino-2-(ethylamino)-6-(trifluoromethyl)pyridine

A solution of 2-(ethylamino)-3-nitro-6-(trifluoromethyl) pyridine (1.1 g, 4.9 mmol) in MeOH (40 mL) was stirred overnight at room temperature under hydrogen (1 atm.) in the presence of 20% Pd(OH)$_2$/C (100 mg). The catalyst was removed by filtration through diatomaceous earth. The filtrate was concentrated under reduced pressure to give the title compound as an orange oil (1 g).

c) 2-Chloro-N-{2-(ethylamino)-6-(trifluoromethyl)-3-pyridinyl}-5-bromo-3-pyridinecarboxamide To a cooled solution of 3-amino-2-(ethylamino)-6-trifluoromethyl pyridine (1 g, 4.9 mmol) in MeCN (24 mL) was added solid NaHCO$_3$ (906 mg, 11 mmol). After 5 min, crude 5-bromo-2-chloro-3-pyridinecarbonyl chloride (prepared from 5-bromo-2-hydroxy-3-pyridinecarboxylic acid and SOCl$_2$ [as described by T. W. Gero et al. in Synth. Commun. 1989,19,553–559 (incorporated herein by reference) but with omission of the aqueous work-up] was added (1 equiv., 4.9 mmol). After 2 h, the reaction mixture was poured over ice/H2O (1.5 L) and the resulting solid was filtered, rinsed with H$_2$O and then hexane. After drying under reduced pressure overnight, the title compound was obtained as a light brown solid (1.6 g, 77% yield).

d) 8-Bromo-5,11-dihydro-11-ethyl-2-(trifluoromethyl)-6H-dipyrido[3,2-b:2',3'-e][1,4]diazepin-6-one To a solution of 2-chloro-N-{2-(ethylamino)-6-(trifluoromethyl)-3-pyridinyl}-5-bromo-3-pyridinecarboxamide (766 mg, 1.8 mmol) in DMF (18 mL) was added NaH (137 mg, 5.4 mmol). The reaction was stirred at 80° C. After 1 h the reaction was allowed to cool to room temperature, and then was poured in water (20 mL). The resulting mixture was extracted with EtOAc (3×). The combined organic layer was successively washed with water and brine, dried (MgSO$_4$), filtered and concentrated under reduced pressure. The residue was purified by flash chromatography (hexane:EtOAc, 7:3) to give the desired compound (200 mg, 28% yield) as a yellow solid.

e) 8-Bromo-5,11-dihydro-11-ethyl-5-methyl-2-(trifluoromethyl)-6H-dipyrido[3,2-b:2',3'-e][1,4]diazepin-6-one To a solution of the 8-bromo-5,11-dihydro-11-ethyl-2-(trifluoromethyl)-6H-dipyrido[3,2-b:2',3'-e][1,4]diazepin-6-one (200 mg, 0.52 mmol) in DMF (2.6 mL) was added NaH (20 mg, 0.78 mmol), and the mixture was heated to 50° C. for 30 min. The reaction mixture was cooled to room temperature and treated with MeI (97 µL, 1.56 mmol). After 16 h, the reaction mixture was diluted with water. The resulting mixture was extracted with EtOAc (3×). The combined organic layer was successively washed with water and brine, dried (MgSO$_4$), filtered and concentrated under reduced pressure. The residue was purified by flash chromatography (hexane:EtOAc, 8.5:1.5) to give the title compound (110 mg 53% yield) as a white foam.

f) 5,11-Dihydro-11-ethyl-5-methyl-8-(2-propenyl)-2-(trifluoromethyl)-6H-dipyrido[3,2-b:2',3'-e] [1,4]diazepin-6-one Allyltributyltin (98 µL, 0.32 mmol) and Pd(Ph$_3$P)$_4$ (16 mg, 0.02 mmol) were added to a degassed (N$_2$ through solution for 30 min) solution of 8-bromo-5,11-dihydro-11-ethyl-5-methyl-2-(trifluoromethyl)-6H-dipyrido[3,2-b:2', 3'-e] [1,4]diazepin-6-one (11 mg, 0.27 mmol) in DMF (1.4 mL) at room temperature. The mixture was stirred at 90° C. for 1.5 h then was cooled to room temperature and concentrated under reduced pressure. The residue was purified by flash chromatography (hexane:EtOAc, 8:2 to 7:3) to give the title compound (101 mg, 99% yield).

g) 5,11-Dihydro-11-ethyl-8-(2-hydroxyethyl)-5-methyl-2-(trifluoromethyl)-6H-dipyrido[3,2-b:2',3'e][1,4]diazepin-6-one A stream of ozonised oxygen was bubbled through a cold (−78° C.) solution of 5,11-dihydro-11-ethyl-5-methyl-8-(2-propenyl)-2-(trifluoromethyl)-6H-dipyrido[3,2-b:2',3'-e][1, 4]diazepin-6-one (100 mg, 0.27 mmol) in CH$_2$Cl$_2$ (2.7 mL) and MeOH (2.7 mL) for 2.5 h. A stream of N$_2$ was next bubbled through the solution for 15 min and then solid NaBH$_4$ (52 mg, 1.4 mmol) was added to the solution. The reaction mixture was allowed to warm to room temperature. After 1 h, aqueous saturated NH$_4$Cl (5 mL) was added and the mixture was stirred at room temperature for 2 h. The reaction mixture was diluted with CH$_2$Cl$_2$ and the aqueous layer was re-extracted with CH$_2$Cl$_2$. The combined organic layer was successively washed with water and brine, dried (MgSO$_4$), filtered and concentrated under reduced pressure. The residue was purified by flash chromatography (EtOAc:hexane: 75:25 to EtOAc 100%) to give the title compound (60 mg 59% yield) as a white solid.

h) 5,11-Dihydro-11-ethyl-5-methyl-8-{2-(4-quinolinyloxy) ethyl}-2-(trifluoromethyl)-6H-dipyrido[3,2b:2',3'-e] [1,4] diazepin-6-one Diethyl azodicarboxylate (DEAD) (38 µL, 0.24 mmol) was added dropwise to a solution of 5,11-dihydro-11-ethyl-8-(2-hydroxyethyl)-5-methyl-2-(trifluoromethyl)-6H-dipyrido[3,2-b:2',3'-e] [1,4]diazepin-6-one (58 mg, 0.16 mmol), 4-hydroxyquinoline (35 mg, 0.24 mmol) and Ph$_3$P (62 g, 0.24 mmol) in THF (1.6 mL) at room temperature. The mixture was stirred at room temperature for 1 h then was concentrated under reduced pressure. The residue was purified by flash chromatography (EtOAc:MeOH; 95:5) to give the title compound (24 mg, 31% yield) as a white solid: MS (ESI) m/z 494, 495 (MH)$^+$.

i) 5,11-Dihydro-11-ethyl-5-methyl-8-{2-{(1-oxido-4-quinolinyl)oxy}ethyl}-2-(trifluoromethyl)-6H-dipyrido[3, 2-b:2',3'-e] [1,4] diazepin-6-one Solid mCPBA (80–85%, m-chloroperbenzoic acid) (16 mg, 0.08 mmol) was added to a solution of 5,11-dihydro-11-ethyl-5-methyl-8-{2-(4-quinolinyloxy)ethyl}-2-(trifluoromethyl)-6H-dipyrido[3,2-b:2',3'-e][1,4]diazepin-6-one (22 mg, 0.04 mmol) in CH$_2$Cl$_2$ (0.5 mL) at room temperature. The mixture was stirred at room temperature for 2.5 h then diluted with CH$_2$Cl$_2$. The resulting solution was successively washed with aqueous 10% Na$_2$S$_2$O$_3$, aqueous saturated NaHCO$_3$ and brine, dried (MgSO$_4$), filtered and concentrated under reduced pressure. The residue was purified by flash chromatography (MeOH:CHCl$_3$, 5% to 10%) to give the title compound (11 mg, 52% yield) as a white solid: MS (ESI) m/z 511 (MH)$^+$.

TABLE 1

Compounds of formula I

[Structure: tricyclic compound with R4, R5, N5, C6=O, R2, N1, N11-R11, positions 2,3,4,7,8,9,10, with substituent at position 8: -CH2CH2-O-Q]

| Table 1 Entry # | R² | R⁴ | R⁵ | R¹¹ | Q |
|---|---|---|---|---|---|
| 1 | Cl | Me | H | Et | 4-methylquinolinyl |
| 2 | Cl | H | Me | Et | 4-methylquinolinyl |
| 3 | H | Me | H | CycPr | 4-methylquinolinyl |
| 4 | F | H | Me | Et | 4-methylquinolinyl |
| 5 | F | Me | H | CycPr | 4-methylquinolinyl |
| 6 | Cl | H | Me | CycPr | 4-methylquinolinyl |
| 7 | F | Me | H | Et | 4-methylquinolinyl |
| 8 | H | Me | H | Et | 4-methylquinolinyl |

TABLE 1-continued

Compounds of formula I

| Table 1 Entry # | R² | R⁴ | R⁵ | R¹¹ | Q |
|---|---|---|---|---|---|
| 9 | F | Me | H | Et | 4-methylquinolinyl N-oxide |
| 10 | Cl | H | Me | CycPr | 4-methylquinolinyl N-oxide |
| 11 | F | H | Me | Et | 4-methylquinolinyl N-oxide |
| 12 | H | Me | H | Et | 4-methylquinolinyl N-oxide |
| 14 | Cl | Me | H | Et | 4-methylquinolinyl N-oxide |
| 15 | H | Me | H | CycPr | 4-methylquinolinyl N-oxide |
| 17 | Cl | H | Me | Et | 4-methylquinolinyl N-oxide |

TABLE 1-continued

Compounds of formula I

| Table 1 Entry # | R² | R⁴ | R⁵ | R¹¹ | Q |
|---|---|---|---|---|---|
| 18 | F | H | Me | Et | 5-methylquinoline N-oxide |
| 19 | Cl | Me | H | Et | 5-methylquinoline N-oxide |
| 20 | Cl | H | Me | Et | 5-methylquinoline N-oxide |
| 21 | H | H | Me | Et | 4-methylquinoline N-oxide |
| 22 | Cl | H | H | Et | 4-methylquinoline N-oxide |
| 23 | F | Me | H | Et | 4-methylquinoline N-oxide |
| 24 | H | H | Me | Et | 4-methylquinoline |
| 25 | Cl | Me | H | Et | 4-methylquinoline |
| 26 | H | H | Et | Et | 4-methylquinoline |
| 27 | H | H | Et | Et | 4-methylquinoline N-oxide |
| 28 | Me | H | Me | Et | 4-methylquinoline N-oxide |
| 29 | CF₃ | H | H | Et | 4-methylquinoline N-oxide |

REVERSE TRANSCRIPTASE (RT) ASSAYS

Assay Theory:

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay and is based upon the observation that reverse transcriptase is able to use a synthetic template poly r(C) primed with a biotinylated oligo d(G) to transcribe a radio-labelled DNA strand utilising 3H-dGTP as a substrate. The assay described below utilises the wild-type enzyme (which is the predominant form of the enzyme observed in patients infected with HIV-1) and can also be used with mutant RT enzymes (for example, Y181C, prepared by site-directed mutagenesis in which the tyrosine residue at codon 181 has been replaced by a cysteine residue) in analogous assay conditions. This assay allows compounds to be evaluated for their effectiveness at inhibiting the mutant enzymes.

Materials:

a) Preparation of the Enzyme

Some HIV-1 IIIB clone BH10 RT mutants were provided by Dr. C. -K. Shih (Boebringer Ingelheim Pharmaceuticals Inc., U.S.A.) in the vector pKK233-2 (Pharmacia). Briefly an HIV RT clone pKRT2 containing only the RT p66 gene regulated by the lac operon/trc promoter was obtained from Dr. W. Summers (Yale University) (2). A variety of specific amino acid substitutions were introduced into the wild-type RT gene by site-directed mutagenesis. RT clones were subcloned into the pKK233–2 bacterial expression vector. Clones provided included wild-type, Val106Ala, Tyr181Cys, Tyr188Cys, Tyr188Leu, Gly190Ala and Pro236Leu. Others were made in-house by site-directed mutagenesis of the pKK233-2 RT clones including Lys103Asn, Lys103Asn/Tyr181Cys, Lys103Asn/Leu100Ile, Lys103Asn/Pro225His, and Lys103Asn/Val108Ile.

b) Purification of Enzyme

Purification of recombinant reverse transcriptase was performed using a combination of methods previously described (3). A single colony from a fresh plate of transformed JM109 cells was used to initiate growth of a pre-culture grown o/n at 37° C. Two liters of growth medium were inoculated with this pre-culture. At $OD_{600}$~1.5 (5–6 h at 37° C.). RT gene expression was induced with IPTG (1 mM final), and the fermentation was continued for a few more hours at 37° C. After centrifugation, supernatants were discarded while cell pellets were pooled and stored at −80° C. until purification. Cells were thawed at 4° C. overnight and suspended in lysis buffer (MES 50 mM pH 6, EDTA 1 mM, 10% v/v glycerol, 0.02% w/v OBG, 0.02% w/v sodium azide). Lysozyme was added and the mixture was incubated on ice for 40 minutes. After homogenization using a Dounce in presence of lysozyme and sonication, the cells were centrifuged for 30 minutes. Supernatant (S1) was saved and stored at 4° C. The centrifuged pellet was resuspended in extraction buffer (MES 50 mM pH 6, $KPO_4$ 50 mM pH 6, KCl 100 mM, 10% v/v glycerol, 0.02% w/v OBG, 0.02% w/v sodium azide) and stirred for 30 minutes at 4° C. This second mixture was centrifuged again and the supernatant (S2) was saved. The above procedure was repeated 2 more times saving supernatants S3 and S4 and one last extraction was performed overnight (S5). Polymin P (0.005% final) was added to the combined supernatants to remove nucleic acids, This solution was stirred for 75 minutes at 4° C. and centrifuged for 1 h. The supernatant (SS1) was precipitated on ice with 20% w/v ammonium sulfate and stirred for 1 h at 4° C. The mixture was then centrifuged and the resulting supernatant (SS2) was precipitated with additional 40% w/v ammonium sulfate (60% total), stirred for 1 h and centrifuged again. The final pellet (P1) was stored overnight at 4° C. before undergoing purification the following day. All steps of the purification were performed at 4° C. unless otherwise stated Pellet (P1) was resuspended into MES 50 mM pH 6, $KPO_4$ 10 mM pH 6, KCl 100 mM, 10% w/v glycerol, 0.02% w/v OBG, 0.02% w/v sodium azide. The suspension was dialysed against the same buffer overnight using 12–14 kD MWCO dialysis tubing. The dialysate was centrifuged and the supernatant was filtered through Millex-PF 0.8 μm filter units. The filtered sample was loaded on a Hydroxy Apatite column (30-mL bed volume) and washed with the same buffer. The bound enzyme was eluted with 220 mL of a linear gradient of 10 to 300 mM $KPO_4$ in the above buffer. The fractions containing p66/p51 heterodimer (as determined by SDS-PAGE 8% and Western blotting) were pooled for the next column. The RT containing fractions were diluted two-fold with Bis-Tris propane 50 mM pH 7.0, 0.02% w/v OBG, 10% v/v glycerol, 0.02% w/v sodium azide and loaded on a Hi-Trap Heparin Sepharose column (5-mL bed volume) and washed with the same buffer. The bound RT was then eluted with 75 mL of a linear gradient of 0 to 1 M ammonium sulfate in the same buffer. RT-containing fractions were pooled according to SDS-PAGE and Western blotting analyses. Protein concentration of this pool was determined by the Bradford method using BSA as standard. The final enzyme preparation was dialyzed in MES 50 mM pH 6, $KPO_4$ 300 mM pH 6, KCl 175 mM, 10% v/v glycerol, 0.02% w/v sodium azide and aliquoted and frozen at −80° C.

Assay Procedure:

The radiometric enzyme assay has been adapted to a 96-well microtiter plate format and uses streptavidin scintillation proximity beads. The assay is briefly described below. The HIV-1 RT enzyme was thawed and appropriately diluted in Tris/HCl 50 mM pH 7.8 containing NaCl 60 mM, $MgCl_2$ hexahydrate 2mM, DTT 6 mM, GSH 2 mM and 0.02% w/v Chaps to give ≈3 nM enzyme. To 30 μL of this enzyme solution was added 10 μL of inhibitor solution (50 μM to 2.5 nM inhibitor in same assay buffer as above containing 15% v/v DMSO). The plate was pre-incubated for 15 minutes at room temperature before proceeding to the next step. In this pre-incubation step, the highest and lowest inhibitor concentrations were 12.5 μM and 0.62 nM respectively and the concentration of DMSO was 3.75% v/v. Then the enzymatic reaction was initiated by addition of 10 μL of substrates solution. The final reaction mixture contained Tris/HCl 50 mM pH 7.8, NaCl 60 mM, $MgCl_2·6H_2O$ 2 mM, DTT 6 mM, GSH 2 mM, Chaps 0.02% w/v DMSO 3% v/v, Poly rC 179 nM, Biotin $dG_{15}$ 18 nM, dGTP 288 nM, $^3$H-dGTP 71 nM, and 1–2 nM enzyme.

In this incubation step, the highest and lowest inhibitor concentrations were 10 μM and 0.5 nM respectively. After addition of substrates, the plate was covered with a plastic seal and incubated for 1 hour at 37° C. in a dry incubator. Then the reaction was quenched by addition of 75 μL of EDTA 0.5M containing 5 mg/mL of streptavidin scintillation proximity beads.

The plate was shaken for 2 minutes at medium speed and incubated 1 hour at room temperature. Then 75 μL of cesium chloride 7 M solution was added, the plate was shaken for 2 minutes at medium speed and incubated again for 1 hour at room temperature. The plate was then covered with a plastic seal and counted using the TopCount-NXT™ Microplate Scintillation & Luminescence Counter, (Packard). Each well was counted for 60 seconds.

Each row contained at its extremities a blank and a control well.

The calculation for percent inhibition is as follows:

$$\% \cdot \text{inhibition} = \left(1 - \left[\frac{cpm \cdot \text{well} - cpm \cdot \text{blank}}{cpm \cdot \text{control} - cpm \cdot \text{blank}}\right]\right) * 100$$

Using the above assay, compounds of the invention were tested for inhibition of RT wild-type (WT) and mutant enzymes. The results are listed in Table 2, as $IC_{50}$ (nM).

To confirm the ability of these compounds to inhibit HIV replication, they were also tested in the human T-Cell Culture (Syncytia) Assay described below.

ELISA assay for assessment of activity in cell culture

Compounds of the invention were tested for their ability to inhibit HIV replication in cell culture in a 96-well plate assay. Complete RPMI 1640, consisting of RPMI 1640+ 10% fetal bovine serum, 10 μg/ml gentamycin and 10 μM β-mercaptoethanol was used for dilution of the compound as well as cell growth medium. The T lymphocyte cell line C8166 was infected at a multiplicity of infection of 0.001 with viruses coding for wild-type and mutant reverse transcriptase. Cells were then incubated for three days in the presence of serial dilutions of the compounds of the invention. The supernatant was pooled from eight replica wells and the concentration of extracellular p24 was determined using a commercially available HIV-1 p24 antigen assay kit (Beckman-Coulter®). The level of inhibition (% inhibition) was calculated with the following equation:

$$\% \cdot \text{inhibition} = \left(1 - \left[\frac{p24pg/mL \cdot \text{inhibitor}}{p24pg/mL \cdot \text{control}}\right]\right) * 100$$

The results are listed in Table 3, as $EC_{50\ (nM)}$.

Specificity Assays

In order to assess the specificity of the enzyme inhibitory activity of the compounds provided by the invention, a few were tested, for their ability to inhibit other viral polymerases (such as Hepatitis C virus and Respiratory Syncytial virus RNA-dependent RNA polymerases) as well as mammalian polymerases (such as Calf Thymus RNA-dependent DNA polymerase and Human telomerase) using known assay methods. None of the compounds so tested was observed to possess any significant inhibitory activity against these enzymes. These results indicate that the enzyme inhibitory activity of the compounds provided by the invention is directed rather specifically against HIV-1 RT.

REFERENCES (INCORPORATED HEREIN BY REFERENCE)

1. Benn, S., et al. Science 230:949,1985.
2. D'Aquila, R. T. and Summers, W. C. J. Acq. Imm. Def. Syn. 2:579, 1989.
3. a) Warren, T. C. et al. Protein Expression & Purification 3:479, 1992; b) Kohlstaedt, L. A. Science 256(5065): 1783,1992.

TABLE 2

Inhibition of Wild-type and mutant strains of RT for compounds of formula I

| compound no. (see Table 1) | $IC_{50}$ WT RT (nM) | $IC_{50}$ K103N (nM) | $IC_{50}$ Y181C (nM) | $IC_{50}$ V106A (nM) | $IC_{50}$ P236L (nM) | $IC_{50}$ Y188L (nM) | $IC_{50}$ G190A (nM) | $IC_{50}$ K103N/ Y181C (nM) | $IC_{50}$ K103N/ P225H (nM) | $IC_{50}$ Y188C (nM) | $IC_{50}$ K103N/ V108I (nM) | $IC_{50}$ K103N/ L100I (nM) |
|---|---|---|---|---|---|---|---|---|---|---|---|---|
| 1 | 10.5 | 19 | 20 | 132 | | 2740 | | 52 | 31.2 | | 29 | 28.5 |
| 2 | 5.5 | 28.5 | 25 | 148 | 50.5 | 258 | 14.5 | 24.5 | 27 | 7.1 | 31 | 46 |
| 3 | 16.5 | 45 | 73 | 79 | | 3236 | | 612 | 56 | | 47 | 124 |
| 4 | 11 | 22.5 | 26 | 206 | | 520 | | 52 | 27 | | 32 | 108 |
| 5 | 19 | 37.5 | 76 | 61 | | 2541 | | 536 | 38 | | 38 | 98 |
| 6 | 25 | | | | | | | | | | | |
| 7 | 9.8 | 26 | 38 | 74 | | 4318 | | 199 | 46 | | 45 | 98 |
| 8 | 10 | 37 | 43 | 190 | | 7511 | | 301 | 67 | | 63 | 135 |
| 9 | 14 | 23 | 43 | 98 | | 3395 | | 175 | 25 | | 58 | 88 |
| 10 | 41 | 67 | 206 | 1372 | | 1422 | | 710 | | | 255 | 229 |
| 11 | 9.5 | 18 | 27 | 336 | 56 | 661 | 19 | 55 | 15 | 6.6 | 55 | 102 |
| 12 | 12 | 31 | 38 | 121 | | >10000 | | 212 | 38 | | 75 | 124 |
| 14 | 15 | 19 | 28 | 77 | | 2298 | | 61 | 30 | | 59 | 24 |
| 15 | 61 | 66 | 226 | 206 | | >10000 | | 1522 | 93 | | 215 | 270 |
| 17 | 14 | 25 | 29 | 319 | 60 | 198 | 25 | 48 | 23 | 8.1 | 83 | 40 |
| 18 | 11 | 37 | 41 | 737 | | 1167 | | 146 | 20 | | 96 | 158 |
| 19 | 7 | 25 | 20 | 89 | | 3938 | | 91 | 16 | | 56 | 27 |
| 20 | 10 | 36 | 22 | 661 | | 439 | | 51 | 17 | | 64 | 44 |
| 21 | 17 | 44 | 51 | 1106 | 129 | 1357 | 26 | 95 | 40 | 9.9 | 120 | 168 |
| 22 | 41 | | | 2493 | | 2990 | | 336 | | | | |
| 23 | 6.1 | | | 105 | | 5614 | | 247 | | | | |
| 24 | 5.6 | | | 344 | | 627 | 25 | 70 | | | | 169 |
| 25 | 8 | 19 | 17 | 84 | | 2537 | | 64 | 23 | | 38 | 28 |
| 26 | 8.9 | 40 | 51 | 1745 | | 5204 | | 200 | 85 | | 147 | 443 |
| 27 | 38 | | | 2271 | | 5335 | | 299 | | | | |
| 28 | 19 | | | 605 | | 1190 | 25 | 141 | 25 | 9.0 | 35 | 28 |
| 29 | 35 | | | 893 | | 578 | | 84 | | | | |

TABLE 3

Inhibition of wild type and mutant strains of HIV in cell cultures by compounds of formula I

| compound no. (see Table 1) | $EC_{50}$ WT RT (nM) | $EC_{50}$ K103N (nM) | $EC_{50}$ Y181C (nM) | $EC_{50}$ V106A (nM) | $EC_{50}$ Y188L (nM) | $EC_{50}$ K103N/ Y181C (nM) | $EC_{50}$ K103N/ P225H (nM) | $EC_{50}$ K103N/ V108I (nM) | $EC_{50}$ K103N/ L100I (nM) |
|---|---|---|---|---|---|---|---|---|---|
| 1 | 2.6 | | | | | | | | |
| 2 | 2.2 | | | | | | | | |
| 3 | 1.3 | | | | | | | | |
| 4 | 0.98 | | | | | | | | |
| 5 | 0.83 | | | | | | | | |
| 6 | | | | | | | | | |
| 7 | 1.1 | | | | | | | | |
| 8 | 0.93 | | | | | | | | |
| 9 | 0.92 | | | 5 | 118 | 7.6 | | | |
| 10 | | | | | | | | | |
| 11 | 0.34 | 2 | 4.1 | 28 | 52 | 7.5 | 2.0 | 3.9 | 3.2 |
| 12 | 0.26 | 2.8 | 2.7 | 12.4 | | | 1.5 | 5.0 | 2.9 |
| 14 | 0.67 | | | | | | | | |
| 15 | | 1.5 | 2.8 | 24 | 58 | 2.3 | 1.2 | 2.7 | 1.2 |
| 17 | 0.34 | | | | | | | | |
| 18 | 0.34 | | | | | 9.5 | | | |
| 19 | 0.37 | | | | | 22 | | | |
| 20 | 0.40 | | | | | 11 | | | |
| 21 | 0.53 | 3.5 | 4.8 | 65 | 67 | 4.3 | 2.9 | 5.0 | 5.9 |
| 22 | | | | | | | | | |
| 23 | | | | | | | | | |
| 24 | | | | | | | | | |
| 25 | 2.2 | | | | | | | | |
| 26 | 2.2 | | | | | | | | |
| 28 | 1.3 | 2.3 | 2.6 | 42 | 70 | 7.5 | | | |
| 29 | 1.6 | | | 83 | 65 | 3.5 | | | |

What is claimed is:

1. A compound of the formula I:

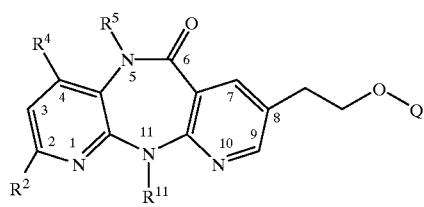

wherein $R^2$ is selected from the group consisting of H, F, Cl, $C_{1-4}$ alkyl, $C_{3-4}$ cycloalkyl and $CF_3$;

$R^4$ is H or Me;

$R^5$ is H, Me or Et, with the proviso that $R^4$ and $R^5$ are not both Me, and if $R^4$ is Me then $R^5$ cannot be Et;

$R^{11}$ is Et; and

Q is selected from the group consisting of:

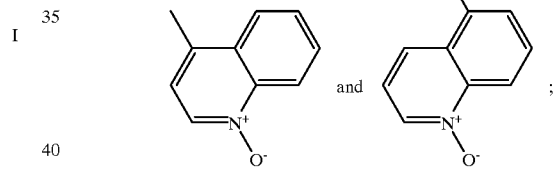

or a pharmaceutically acceptable salt thereof.

2. A compound according to claim 1, wherein Q is selected from the group consisting of:

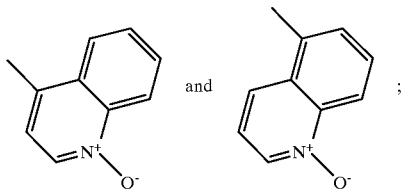

or a pharmaceutically acceptable salt thereof.

3. A compound according to claim 1, wherein Q is:

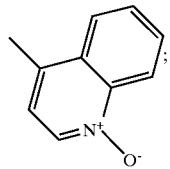

or a pharmaceutically acceptable salt thereof.

4. A compound according to claim 1, wherein $R^5$ is Me, or a pharmaceutically acceptable salt thereof.

5. The compound:

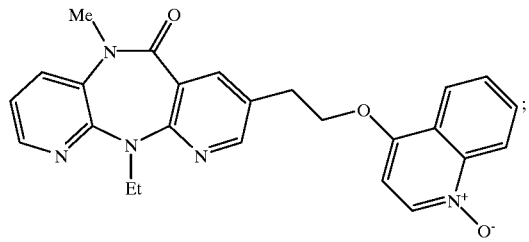

or a pharmaceutically acceptable salt thereof.

6. The compound:

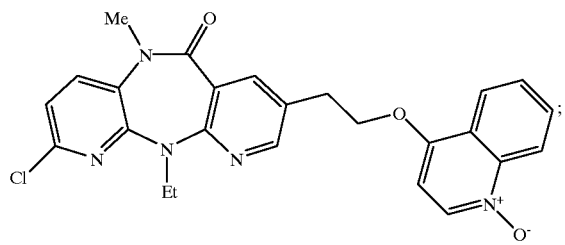

or a pharmaceutically acceptable salt thereof.

7. The compound:

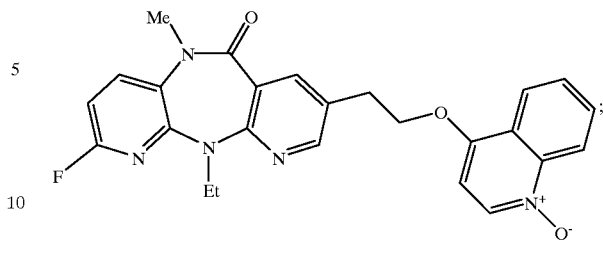

or a pharmaceutically acceptable salt thereof.

8. A method for the treatment of HIV infection, comprising administering to a patient an HIV inhibiting amount of a compound of formula I according to claim 1, or a pharmaceutically acceptable salt thereof.

9. A pharmaceutical composition for the treatment of HIV infection, comprising a compound of formula I according to claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 6,420,359 B1
DATED : July 16, 2002
INVENTOR(S) : Bruno Simoneau

It is certified that error appears in the above-identified patent and that said Letters Patent is hereby corrected as shown below:

Column 13,
Lines 13-15, change "5,11-Dihydro-11-ethyl-5-methyl-8-{2-(4-quinolinytoxy)ethyl}-6H-dipyrido[3,2-b:2',3'-e] [1,4]diazepin-6-one" to -- 5,11-Dihydro-11-ethyl-5-methyl-8-{2-(4-quinolinyloxy)ethyl}-6H-dipyrido[3,2-b:2',3'-e] [1,4]diazepin-6-one --.

Column 20,
Lines 54-56, change "5,11-Dihydro-11-ethyl-2-fluoro4-methyl-8-{2-(4-quinolinyloxy)ethyl}-6H-dipytido[3,2-b:2',3'-e] [1,4]diazepin-6-one" to -- 5,11-Dihydro-11-ethyl-2-fluoro-4-methyl-8-{2-(4-quinolinyloxy)ethyl}-6H-dipyrido[3,2-b:2',3'-e] [1,4]diazepin-6-one --

Column 22,
Lines 26-28, change "11-(Cyclopropyl)-5,11-dihydro-2-fluoro-4-methyl-8-{2-(4-quinolinyloxy)-ethyl}-6H-dipytido[3,2-b:2',3'-e] [1,4]diazepin-6-one" to -- 11-(Cyclopropyl)-5,11-dihydro-2-fluoro-4-methyl-8-{2-(4-quinolinyloxy)-ethyl}-6H-dipyrido[3,2-b:2',3'-e] [1,4]diazepin-6-one --

Column 24,
Lines 63-65, change "5,11-Dihydro-1l-ethyl-5-methyl-8-{2-{(1-oxido-4-quinolinyl)oxy}ethyl}-6H-dipytido[3,2-b:2',3'-e] [1,4]diazepin-6-one" to -- 5,11-Dihydro-11-ethyl-5-methyl-8-{2-{(1-oxido-4-quinolinyl)oxy}ethyl}-6H-dipyrido[3,2-b:2',3'-e] [1,4]diazepin-6-one --

Column 27,
Lines 5-7, change "11-Cyclopropyl-5,11-dihydro-11-ethyl-4-methyl-8-{2-{(1-oxido-4-quinolinyl)oxy)ethyl}-6H-dipyrido[3,2-b:2',3'-e][1,4]diazepin-6-one"
to -- 11-Cyclopropyl-5,11-dihydro-4-methyl-8-{2-{(1-oxido-4-quinolinyl)oxy}ethyl}-6H-dipyrido[3,2-b:2',3'-e][1,4]diazepin-6-one --
Lines 9-11, change "11-cyclopropyl-5,11-dihydro-11-4-methyl-8-{2-(4-quinolinyloxy)ethyl}-6H-dipyrido[3,2-b:2',3'-e] [1,4]diazepin-6-one" to -- 11-cyclopropyl-5,11-dihydro-4-methyl-8-{2-(4-quinolinyloxy)ethyl}-6H-dipyrido[3,2-b:2',3'-e] [1,4]diazepin-6-one --

UNITED STATES PATENT AND TRADEMARK OFFICE
CERTIFICATE OF CORRECTION

PATENT NO. : 6,420,359 B1
DATED : July 16, 2002
INVENTOR(S) : Bruno Simoneau

It is certified that error appears in the above-identified patent and that said Letters Patent is hereby corrected as shown below:

Column 28,
Lines 48-49, change "5,11-Dihydro-5,11-diethyl-8-{2-(4-quinolinyloxy)ethyl}-6H-dipyrido[3,2-b:2',3'-e] [4]diazepin-6-one" to -- 5,11-Dihydro-5,11-diethyl-8-{2-(4-quinolinyloxy)ethyl}-6H-dipyrido[3,2-b:2',3'-e] [1,4]diazepin-6-one --
Lines 55-57, change "5,11-Dihydro-5,11-diethyl-8-{2-{(1-oxido-4-quinolinyl)oxy}ethyl}-6H-dipyrtido[3,2-b:2;3'-e] [1 ,4]diazepin-6-one" to -- 5,11-Dihydro-5,11-diethyl-8-{2-{(,4-oxido-4-quinolinyl)oxy}ethyl}-6H-dipyrido[3,2-b:2',3'-e] [1,4] diazepin-6-one --

Column 36,
Line 50, Table row which corresponds to Entry # 29 change the value for R5 from "H" to -- CH3 --.

Signed and Sealed this

Seventeenth Day of August, 2004

JON W. DUDAS
*Acting Director of the United States Patent and Trademark Office*